(12) United States Patent
Sandrin et al.

(10) Patent No.: US 11,571,182 B2
(45) Date of Patent: Feb. 7, 2023

(54) SYSTEM FOR CHARACTERIZING TISSUE AND ASSOCIATED METHOD

(71) Applicant: ECHOSENS SA, Paris (FR)

(72) Inventors: Laurent Sandrin, Bourg-la-Reine (FR); Hugo Loree, Paris (FR)

(73) Assignee: ECHOSENS SA, Paris (FR)

( * ) Notice: Subject to any disclaimer, the term of this patent is extended or adjusted under 35 U.S.C. 154(b) by 297 days.

(21) Appl. No.: 16/522,804

(22) Filed: Jul. 26, 2019

(65) Prior Publication Data
US 2021/0022709 A1    Jan. 28, 2021

(51) Int. Cl.
| | |
|---|---|
| *A61B 8/08* | (2006.01) |
| *G16H 50/20* | (2018.01) |
| *A61B 8/14* | (2006.01) |
| *A61B 90/00* | (2016.01) |
| *A61B 8/00* | (2006.01) |
| *A61B 5/00* | (2006.01) |
| *G06T 7/00* | (2017.01) |

(52) U.S. Cl.
CPC ............... *A61B 8/485* (2013.01); *A61B 8/08* (2013.01); *A61B 8/483* (2013.01); *G16H 50/20* (2018.01); *A61B 5/0064* (2013.01); *A61B 8/14* (2013.01); *A61B 8/4483* (2013.01); *A61B 2090/378* (2016.02); *G06T 7/0012* (2013.01)

(58) Field of Classification Search
CPC .......... A61B 8/485; A61B 8/483; A61B 8/08; A61B 8/14; A61B 2090/378; A61B 8/4483; A61B 5/0064; A61B 5/06; A61B 5/442; A61B 5/6844; A61B 5/0051; G16H 50/20; G16H 40/63; G16H 30/20; G06T 7/0012; G01S 7/5205; G01S 7/52098; G01S 7/52042; G01S 7/52041
See application file for complete search history.

(56) References Cited

U.S. PATENT DOCUMENTS

| | | | |
|---|---|---|---|
| 2002/0010398 A1* | 1/2002 | Bonnefous | ........... A61B 8/0858 600/442 |
| 2011/0130660 A1 | 6/2011 | Cloutier et al. | |

FOREIGN PATENT DOCUMENTS

EP    3750483 A1 * 12/2020    ........... A61B 5/0051

OTHER PUBLICATIONS

Echosens: White Paper: "Vibration-Controlled Transient Elastography" Documenation of 2015 Date using the "Way Back Machine" (Year: 2021).*

(Continued)

*Primary Examiner* — Amanda Lauritzen Moher
*Assistant Examiner* — Delia M. Appiah Mensah
(74) *Attorney, Agent, or Firm* — Pillsbury Winthrop Shaw Pittman LLP

(57) ABSTRACT

A system for characterizing tissue includes a probe that delivers a continuous and periodic mechanical vibration to a tissue of a subject; an ultrasound emitter that emits a sequence of ultrasound shots and an ultrasound receiver that receives corresponding echo signals to track how the tissue is moved by the periodic mechanical vibration delivered to the tissue; and a control module programmed to provide homogeneity information to an operator of the system, the homogeneity information being determined from at least some of the echo signals and being representative of the ability of the tissue to transmit elastic waves and of the homogeneity of the tissue with respect to the propagation of elastic waves.

22 Claims, 14 Drawing Sheets

(56) References Cited

OTHER PUBLICATIONS

Oudry et al. ("Validation of Vibration-Controlled Transient Elastography by means of Dynamic Mechanical Analysis: Application to In vivo / In vitro Porcine Liver.") (Year: 2009).*

Mellema DC, Song P, Kinnick RR, Urban MW, Greenleaf JF, Manduca A, Chen S. Probe Oscillation Shear Elastography (PROSE): A High Frame-Rate Method for Two-Dimensional Ultrasound Shear Wave Elastography. IEEE Trans Med Imaging. Sep. 2016 (Year: 2016).*

Mellema, D. C., "Probe Oscillation Shear Wave Elastography: Initial In Vivo Results in Liver," IEEE Transactions on Medical Imaging, vol. 37, Issue 5, May 2018, 10 pages.

Loree, H., et al., "Hybrid elastography: a new technique for the assessment of tissue stiffness," IEEE International Ultrasonics Symposium (IUS), Oct. 2018, 4 pages.

European Search Report as issued in European Patent Application No. 19188700.9, dated Jan. 2, 2020.

Deffieux, T., et al., "Shear Wave Spectroscopy for In Vivo Quantification of Human Soft Tissues Visco-Elasticity," IEEE Transactions on Medical Imagine, vol. 28, No. 3, Mar. 2009, XP011247217, pp. 313-322.

\* cited by examiner

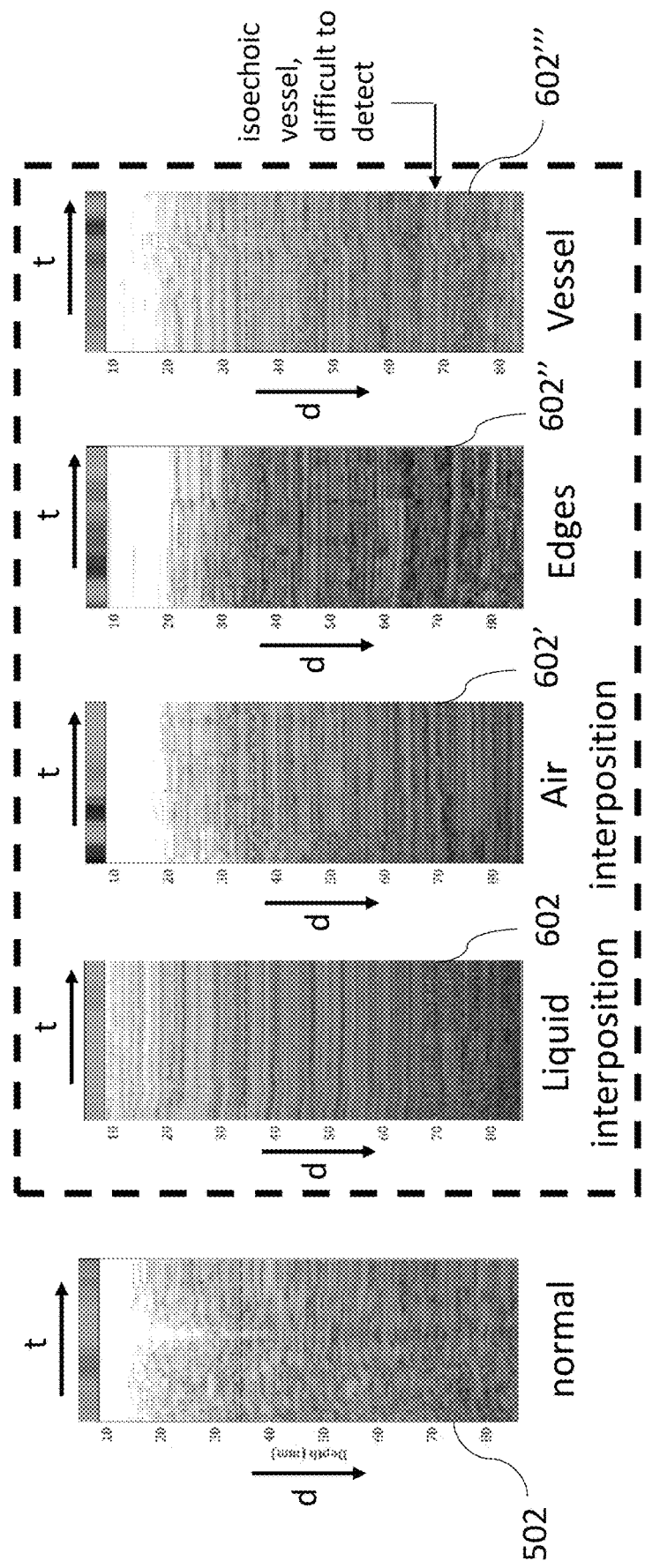

805 = elastic wave propagation map ; transient
808 = elastic wave propagation map ; periodic
809 = phase delay
810 = homogeneity indicator
811 = Amplitude

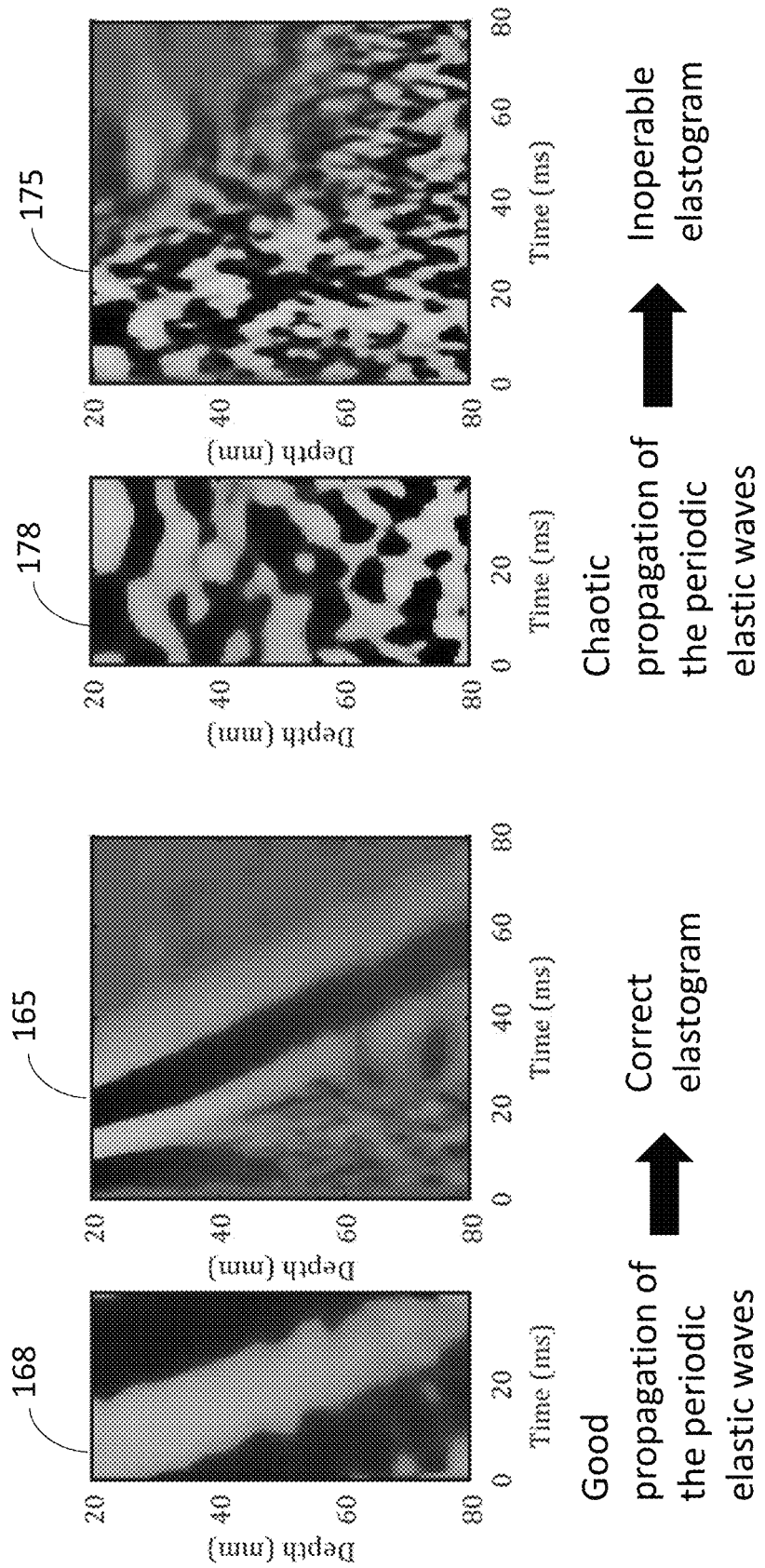

SYSTEM FOR CHARACTERIZING TISSUE AND ASSOCIATED METHOD

CROSS-REFERENCE TO RELATED APPLICATION(S)

The present application is related to PCT application PCT/EP2019/054656 filed Feb. 26, 2019 and to PCT application PCT/EP2019/054658 filed Feb. 26, 2019, which are herein incorporated by reference in their entireties.

TECHNICAL FIELD

The disclosed technology relates to non-invasive tissue characterizing systems and in particular to systems and method for systems for identifying homogeneous tissue in which tissue stiffness or fat content can be non-invasively assessed.

BACKGROUND

It is well known that the stiffness of liver tissue correlates with degrees of liver cirrhosis and other diseases, and that the speed at which a shear wave travels through a region of interest in a subject's liver is directly related to the stiffness of the liver. As a matter of fact, in soft tissues, the stiffness (Young's modulus) can be deduced from the tissue density ($\rho$) and the shear wave speed ($V_s$) using the formulae $E=3\rho V_s^2$. The density of soft tissues is close to 1000 kg/m$^3$. E is expressed in kilopascals and $V_s$ in meter per second (m/s).

To characterize liver or other organ stiffness by shear wave speed measurements, a technique called "harmonic elastography" described for example in the document "Probe Oscillation Shear Wave Elastography: Initial In Vivo Results in Liver" by D. C. Mellema et al., published in IEEE Transactions on Medical Imaging, volume 37, issue 5, May 2018, has been developed.

According to this technique, an array transducer for 2-dimensional B-mode ultrasound imaging is placed on contact with a subject's body and vibrated at a low frequency, typically comprised between 30 Hz and 100 Hz. Ultrasound shots are then emitted to track how the tissue of the subject is moved by this low frequency periodic vibration. An instantaneous 2-dimensional map (a kind of 2D snapshot), showing tissue displacement caused by the low frequency periodic vibration at different points distributed over a 2-dimentional section of the tissue of the subject, and at a same instant, is thus determined (see FIG. 9a of the above mentioned document by D. C. Mellema et al.). A filtered 2-dimensional displacement map is then determined by a complex spatial mode filtering (FIG. 9b, or 8b of Mellema et al.). An inversion algorithm then enables one to derive (from the 2-dimensionnal deformation map) a 2-dimensional map representing the value of the shear wave speed at different points distributed over an entire 2-dimentional section of the tissue (FIG. 8c of Mellema et al.). With this technique, values of the shear wave speed are thus derived from spatial information contained in the instantaneous 2-dimensional displacement map.

But implementing such a method requires a quite complex multibeam ultrasound device, suitable for 2-dimensional ultrasound imaging. And the processing of a single instantaneous 2-dimensional deformation map requires a lot of time, typically 3 vibration periods, according to Mellema et al. This long processing time prevents from sampling a whole vibration period all at once, from a temporal point of view (as explained in the capture of FIG. 3 of Mellema et al.). More precisely, in Mellema, a couple of two ultrasound shots is emitted (every 100 ms) and then, two corresponding ultrasound echo signals are acquired and processed to compute the displacements in the medium at the time the couple of ultrasound shots was emitted. This procedure is then repeated 100 ms later, and so on (with a repetition rate of 10 hertz). Due to the long processing time required to compute and analyze each 2-dimensional deformation map, this procedure cannot be repeated with a higher repetition rate. Therefore, with this technique, a whole vibration period cannot be sampled all at once (as it would require a repetition rate higher than the frequency of the mechanical vibration, namely higher than 100 hertz). Thus, this harmonic elastography technique enables 2-dimensional spatial imaging and is focused on spatial properties of the deformation field, but has a poor temporal resolution and is influenced by tissue motion due to respiration or heart beating for example.

Besides, measuring shear wave speed by harmonic elastography is considered as less reliable and less accurate than by transient elastography, harmonic elastography generally providing over-estimated speed values. Indeed, with harmonic elastography, the periodic mechanical vibration delivered to the subject travels in the subject's tissue as an elastic wave mixing shear waves and compression waves (whose propagation speed is much higher than the one of shear waves), these two components being hardly separable due to the repetitive, continuous nature of the vibration. Furthermore, harmonic elastography measurements can also be skewed by elastic wave reflections inside the tissue, which may create stationary waves patterns (again, due to the repetitive, continuous nature of the vibration).

As a result, the time-harmonic elastography technique described above provides valuable spatial information regarding the structure of the part of the subject's body under examination, thanks to its 2-dimensional imaging capabilities. But it generally provides shear wave speed values that are not very accurate. The main reasons for this lack of accuracy are the combination of shear and compression waves, the influence of diffraction effects due to the large size of the vibration source, the influence of motions such as respiratory motion given that the displacements are usually captured during several cycles of vibration and the out of plane motion that are not measured. These problems result in artefacts on the image that must be interpreted with a lot of caution especially when quantitative measurements are to be provided.

Transient elastography techniques thus seem more adequate than time-harmonic elastography techniques to precisely measure shear wave speed in quite large and homogeneous organs like liver or spleen.

Transient elastography is based on a different approach than the harmonic elastography technique presented above. Instead of recording an instantaneous 2-dimentional map of the tissue deformation (and deriving shear wave speed values from the spatial properties of this map), transient elastography is focused on a spatio-temporal tracking of a transient mechanical pulse delivered to the tissue.

A well known transient elastography system is the FIBROSCAN® system (an ultrasound-based elastography apparatus for measuring the stiffness (or elasticity) and ultrasound attenuation of tissues and organs), produced and sold by Echosens SA of Paris, France, which enables an operator to non-invasively measure liver or other organs stiffness to assess the organ's health.

With the FIBROSCAN® system, an operator places the tip of a probe, that has a rather small diameter (typically comprised between 5 and 10 mm), in contact with the subject's body, in front of the expected area of a subject's liver. The operator then presses a button to make the probe's head deliver to the subject a transient, low frequency mechanical pulse (the spectrum of this pulse is centered on a frequency comprised typically between 10 and 500 hertz). This pulse generates an elastic wave that travels in the subject's body. An ultrasound transducer mounted on the probe's head, in contact with the subject's body, then sends out a number of ultrasound shots into the tissue, with a high repetition rate, of 2 kilohertz at least. The echo signals, corresponding to the backscattering of the different ultrasound shots emitted, are acquired by the probe to track slight movements of the tissue caused by the elastic wave passing through. The tracking is performed using correlation techniques applied to successive echo signals. The detected movements enable one to compound an elastic wave propagation image showing the tissue deformation both as a function of depth d, and as a function of time t (instead of compounding an image showing tissue deformation as a function of two different spatial coordinates, but at a given, fixed instant). FIG. 1 shows such an elastic wave propagation image 105, sometimes referred to as an "elastogram".

Contrary to other elastography methods, the FIBROSCAN®'s probe uses a favorable symmetric design. The ultrasound transducer is a single element transducer mounted on the axis of the vibrator. The axis of the ultrasound transducer coincides with the axis of the vibrator, which is why the displacements induced by the vibrations are largely longitudinal and therefore aligned with the ultrasound beam axis. The measurement of the displacement is significantly improved in such conditions since the out-of-axis displacement are much more difficult to measure using ultrasound. Other elastography devices, especially harmonic ones, are more complex. They use multiple element ultrasound transducer (usually liner or convex arrays) as they aim at providing a map of the mechanical properties in 2D or 3D to locate heterogeneities. The symmetry of these systems is much more complex. Displacements induced by the vibrations are not aligned with the ultrasound beam(s) by design. They require more computation time as they process much more data (several ultrasound lines) and use sophisticated inversion algorithm to assess the mechanical properties in 2D or 3D. Furthermore, they are very slow to operate.

The mechanical pulse delivered by the FIBROSCAN® probe's head generates both a shear wave and of a compression wave. In other words, the elastic wave mentioned above combines a shear wave and a compression wave. But these two waves have very different propagation speeds and, thanks to the transient nature of the mechanical excitation, they can be easily separated in time and identified in the elastic wave propagation image. For example, referring to FIG. 1, this figure shows an elastic wave propagation image 105. In FIG. 1, the compression wave is identified by the reference sign 105C, while the much slower shear wave is identified by the reference sign 105S. Also shown in FIG. 1, is the region of interest (ROI) which is bound by two dashed lines at 25 mm and 65 mm, which corresponds to the depth under the patient skin where liver is typically located. This elastic wave propagation image can thus be used to precisely determine the propagation speed of shear waves in the tissue to be characterized, from which the stiffness of this tissue can be derived. These stiffness results 106 are then provided to the operator, as represented in FIG. 1 which shows different graphs 101, 102, 105 and indicators 103, 106, 107 displayed to the operator by means of a display screen of the FIBROSCAN® system.

The FIBROSCAN® system also enables one to measure the attenuation of the ultrasound signals that are used to track the shear wave, which is useful as ultrasound attenuation correlates with the amount of fat content in the liver (see FIG. 1, ultrasound attenuation results 107).

While the FIBROSCAN® technology works well, it is sometimes difficult for an operator to know if he/she has correctly positioned the probe, in front of an area of homogeneous liver tissue, or if he/she is even aiming the probe at the liver at all. Ribs in front of the liver, blood vessels, liquid pockets (ascites) or other artifacts of non-homogeneous tissue such a cysts or tumors in the liver tissue can produce erroneous measurements of both tissue stiffness and ultrasound attenuation. In addition, an operator may believe that he/she is aiming the probe at the liver, when in fact the probe is too close to the lungs or other internal organs. As a result, the system may not be able to obtain accurate measurements.

To help the operator find an adequate probe position, the FIBROSCAN® system is configured to continuously transmit ultrasound shots and to acquire corresponding echo signals while the operator is searching for an adequate probe position. A-mode and TM-mode graphs are displayed and refreshed in real time to help the operator find the adequate probe position. FIG. 1 shows an example of such an A-mode graph 101 and TM-mode graph 102. A TM-mode graph represents the ultrasound echo signals successively acquired after the ultrasound echo signals have been processed. Processing of the ultrasound echo signals includes, e.g., envelope computation and decimation. The TM-mode graph shown in FIG. 1 is a 2-dimensional image in which each column represents one of the processed ultrasound echo signals acquired. Each column is representative of an instantaneous 1-dimensional image showing, as a function of depth d, how the part of subject's body located that is in alignment with the probe backscatters ultrasound waves. The successive ultrasound echo signals acquired are displayed side-by-side to show the evolution over time t of this 1-dimensional image (this evolution being caused by slight probe movements or by organ movements caused by respiratory motion).

As shown in FIGS. 1 and 2, the TM-graphs may provide useful information regarding the probe 3 positioning. Indeed, when the probe axis x is aligned with a thick, homogeneous part of the liver 4, the TM-graph 402 usually looks like a stack of thin horizontal sheets and has a homogeneous aspect, both horizontally and vertically, as shown in FIG. 4. By contrast, when the probe axis x is close to an edge of the liver 4, the TM-mode graph 202, 302 often has a discontinuous aspect, either horizontally (FIG. 2) or vertically (FIG. 3).

Still, positioning the probe adequately on the basis of the TM-graphs remains quite difficult and requires a proper training of the operator. Furthermore, as will be appreciated by the skilled artisan, an inadequate probe positioning may lead to an inadequate measurement and an inaccurate diagnostic of the patient's condition.

Ultrasound signals displayed in TM-mode or A-mode graphs, though providing some information regarding the position of the probe, are not predictive of the shear wave propagation. In some situations, these graphs may appear adequate, as if the conditions were suitable for transient elastography measurements, whereas no shear wave can actually propagate. This can happen in the presence of liquid interposition (see the TM-mode graph 602 of FIG. 6), air interposition (see the TM-mode graph 602' of FIG. 6), narrow intercostals space, etc. . . . . . Furthermore, though a vessel may not be observed on the ultrasound signals because it is isoechoic, it may disturb the shear wave propagation. FIG. 6 shows a TM-mode graph 602''' acquired in the presence of an isoechoic vessel, in which the vessel remains invisible (the position of this vessel is identified by an arrow).

The guidance using ultrasound data is not good enough because it cannot predict the propagation of the shear wave as ultrasound and elastic are not sensitive to the same conditions. A good ultrasound signal does not always result in a good shear wave propagation. Some elements that influence the shear wave propagation do not affect ultrasound propagation. This is the case of isoechoic parts that can be a vessel, a cyst, a liquid with particles, a stiff or soft tumor, etc.

Due to the limitations of the conventional TM-graph guiding, the operator generally does not find an adequate probe location at the first try he/she attempts to position the probe. In practice, it turns out that the operator often has to trigger the transient elastography measurement several times, testing different positions by trial and error, before finding an adequate position and recording an elastic wave propagation image appropriate to characterize liver stiffness. This is time consuming, all the more that the operator has to hold the probe still and firmly before triggering a transient elastography measurement. As will be appreciated by the skilled artisan, such attempts can be unpleasant for the patient under examination as the patient receives a small mechanical punch each time the operator conducts a measurement. Moreover, such attempts can discourage the operator to find an adequate position and thus increase the failure rate.

It is thus desirable to develop a system for characterizing tissue, suitable for a precise characterization of the viscoelastic properties of this tissue and having improved guiding capabilities compared to the FIBROSCAN® system described above.

SUMMARY

To address at least some of above-mentioned problems, the disclosed technology is directed to a system for identifying homogeneous tissue in a subject or patient. Upon detection of an area of homogeneous tissue, an operator can initiate the measurement of tissue stiffness and/or an ultrasound parameter determination.

In some embodiments, the system comprises:
a probe, to be hold against the body of a subject and that comprises a vibrator to deliver mechanical vibrations to a tissue of the subject;
an ultrasound emitter that is configured to emit a sequence of ultrasound shots and an ultrasound receiver configured to receive corresponding echo signals; and
a control module programmed to make the system executing the following steps:
 a) delivering a continuous and periodic mechanical vibration to the tissue of the subject, the periodic mechanical vibration comprising of a same vibration pattern repeated several times successively over time;
 b) emitting a sequence of ultrasound shots by means of the ultrasound emitter and acquiring corresponding echo signals received by the ultrasound receiver to track how the tissue is moved by the periodic mechanical vibration delivered to the tissue;
 c) providing homogeneity information to an operator of the system, the homogeneity information being determined from at least some of the echo signals acquired in step b), the homogeneity information being representative of the ability of the tissue to transmit elastic waves and of the homogeneity of the tissue with respect to the propagation of elastic waves.

The control module is programmed so that steps b) and c) are executed by the system continuously, several times successively.

The homogeneity information, obtained by tracking how a periodic mechanical vibration travels through the tissue, constitutes a very efficient guiding information that helps the operator find quickly and easily an appropriate probe position, located in front of a thick, homogeneous part of an organ to be characterized.

It will be appreciated that a 2-dimensional elastic waves speed map like the one described in Mellema et al. (or in the document "In vivo time-harmonic ultrasound elastography of the human brain detects acute cerebral stiffness changes induced by intracranial pressure variations" by H. Tzschatzsch et al., published in Scientific Reports, volume 8, article number 17888, 2018, for instance) do not constitute homogeneity information representative of the ability of a tissue to propagate elastic waves and of the homogeneity of the tissue with respect to the propagation of elastic waves. Indeed, such maps do not actually provide information regarding wave propagation, as these maps only represent instantaneous snapshots of the organ under examination In an embodiment according to the disclosed technology, the homogeneity information provided by the system indicates whether spatio-temporal characteristics of a deformation of the tissue, that is caused by the periodic mechanical vibration mentioned above, are those of a wave travelling in a homogeneous medium (the deformation in question being tracked by the echo signals acquired in step b).

As shown in FIGS. 14, 16, 17 and 18, spatio-temporal characteristics of a tissue deformation relative to the propagation of elastic waves through the tissue, that is to say characteristics representative of the variation of this deformation both as a function of time and as a function of at least one spatial coordinate (and thus really representative of the way the elastic wave propagates), reveal the more or less homogeneous nature of the tissue in a very straightforward and easy to apprehend manner. Such spatio-temporal characteristics may comprise data representative of the variation over depth of a phase delay of the periodic deformation of the tissue, for instance. As shown in FIG. 14, this phase delay varies substantially linearly with depth when the tissue is homogeneous, which is easy to identify for the operator. The spatio-temporal characteristics mentioned above may also comprise data representative of the deformation of the tissue, both as a function of depth d and as a function of time t. As shown in FIGS. 16 and 18 (graph 188*a*), a graph representing the deformation of the tissue as a function of depth and as a function of time comprises of diagonal, substantially linear stripes, that can be readily identified by the operator, when the tissue is homogeneous.

The way such periodic elastic waves propagate is much more sensitive to the structure of the tissue and to its elastic properties than TM-mode graphs, as shown in FIG. 18.

The last three columns of the table of FIG. 18 shows TM-mode graphs 182*c*, 182*d*, 182*e*, elastic wave propagation images 188*c*, 188*d*, 188*e* acquired in periodic mode (periodic elastic wave propagation graphs) and elastic wave propagation images acquired in transient mode 185*c*, 185*d*, 185*e* for three different situations, one corresponding to a probe position close to an edge of liver (column c), and the two others being situations with liquid (column d) or air interposition (column e). As can be seen in FIG. 18, in these situations, the TM-mode graphs look as if the situation were appropriate for transient elastography measurements (like in column a), while in fact they are not (see transient elastography images 185c, 185d, 185e). In other words, TM-mode imaging does not discriminate between a proper probe positioning and an improper probe positioning since it cannot accurately detect whether the probe is located close to an edge of the liver or whether there is air or liquid interposed between the probe and the targeted organ. In striking contrast, the periodic elastic wave propagation images 188c, 188d, 188e, which are noisy, comprise numerous irregular fragments, as opposed to one or several diagonal stripes with smooth (substantially linear) edges. Thus, the periodic elastic wave propagation images 188c, 188d, 188e show immediately an adequate probe positioning for transient elastography measurements. Furthermore, the presence of a vessel, even small and isoechoic, which is invisible in the ultrasound signals (see graph 182b of FIG. 18), is readily detectable in an elastic wave propagation image acquired in periodic mode (see graph 188b of FIG. 18).

As will be appreciated by the skilled artisan, a periodic elastic wave propagation image with diagonal stripes substantially uniform and/or with smooth edges, like the image 188a of FIG. 18, indicates immediately that the probe is properly positioned and that the situation is adequate for transient elastography measurement (see the transient elastic wave propagation image 185a of FIG. 18).

It was found that, in practice, the homogeneity information, which is continuously refreshed and provided to the operator, most often enables an operator, even an untrained one, to find a proper probe position right the first time.

Moreover, the periodic mechanical vibration delivered to the subject under examination is less unpleasant to him than the short, transient mechanical pulses that would otherwise be repeatedly triggered by the operator until he/she finds a proper probe position, all the more than the vibration amplitude required for periodic elastic waves monitoring is noticeably smaller than the one required to achieve a transient elastography measurement. In addition, the continuous nature of the mechanical excitation employed in the system of the disclosed technology to guide the operator enables a continuous guiding.

The spatio-temporal monitoring of the deformation caused by the periodic mechanical vibration delivered to the subject can be achieved using a single-beam (single transducer) ultrasound system, with no 2D or 3D imaging capabilities. Indeed, monitoring the propagation of a wave, from a spatio-temporal point of view, can be achieved by monitoring the tissue deformation as a function of time and of one spatial dimension only (namely depth). In other words, a spatio-temporal monitoring can be carried on using a 2 dimensional sampling of the deformation, one dimension being time and the other being depth, instead of using 2 sampling dimensions that are both spatial dimensions (depth and lateral shift, like in Mellema at al.). As will be appreciated by the skilled artisan, using a single-beam ultrasound system, instead of 2D imaging ultrasound system, enables one to process quickly the echo signals acquired, which are mono-dimensionnal from a spatial point of view. This permits to increase the temporal sampling rate with which the elastic deformation of the tissue is tracked. The elastic deformation of the tissue is thus monitored with a higher temporal resolution than in prior art harmonic elastography methods.

Moreover, the high temporal sampling rate enables one to sample a same period, or at least the major part of a same period of the periodic deformation of the tissue, all at once, as a whole. This is very interesting compared to a stroboscopic-like technique in which the periodic deformation of the tissue would be sampled by small parts, sampling a small part (for instance a single instant) of a period, then a small part of a subsequent period and so on to reconstruct, a posteriori, an image showing a whole vibration period (like the propagation image 130 of FIG. 13). Indeed, with a stroboscopic technique, the lag time required to obtain a new, completely refreshed image showing a whole vibration period is much longer than when a same period is sampled all at once with a high sampling rate (in the example of FIG. 13, the lag time is approximately four times longer than when a same period is sampled all at once). More importantly, a temporal image obtained by stroboscopic sampling is often impaired by spurious effects and noise, due in particular to tissue displacement caused by respiration or to slight displacements of the probe. Furthermore, the temporal resolution of propagation images obtained by stroboscopic sampling is generally smaller than when a same period is sampled all at once (the temporal resolution of the propagations images 131 to 134 of FIG. 13, for instance, is better than the one of the propagation image 130).

As will be appreciated by the skilled artisan, graphs showing the periodic deformation of the tissue in a spatiotemporal manner (as those of FIG. 18), as a function of depth and time, are easy to understand as they are. This is quite surprising when compared to prior art harmonic elastography techniques like those of Mellema et al. or Tzschatzsch et al., in which the graphs representing the instantaneous deformation of the tissue (as a function of two spatial coordinates) are hardly comprehensible (see FIG. 9a de Millena et al. or FIG. 3a of Tzschatzsch et al., for example) and require complex post-processing to obtain information useful to an operator (such as a 2D shear wave speed map).

To summarize, a system for characterizing tissue according to the disclosed technology has very good guiding capabilities, enabling an operator to find quickly and easily an area of homogeneous tissue, adequate for transient elastography measurements, or to determine an ultrasound parameter relative to ultrasound wave propagation within the tissue.

To benefit from these guiding capabilities, in an embodiment of a system for characterizing tissue according to the disclosed technology, the control module of the system is further programmed to determine at least one physical property of the tissue comprising one of:
an ultrasound parameter, relative to ultrasound wave propagation within the tissue attenuation value;
a mechanical property of the tissue related to shear wave propagation, determined by transient elastography.

The ultrasound parameter comprises for instance an ultrasound attenuation parameter, that reflects ultrasonic attenuation in the tissue, like a Broadband Ultrasound Attenuation (BUA, usually expressed in dB/cm/MHz), an attenuation measured at a particular frequency (expressed in dB/cm), or a Controlled Attenuation Parameter (CAP). However, this is not limiting as additional parameters could be determined in other embodiments.

The mechanical property of the tissue related to shear wave propagation may be a quantity related to the tissue stiffness, such as the propagation speed of shear waves $V_s$, the shear modulus of the tissue or the Young's modulus E of the tissue. It may also be a quantity related to low frequency shear wave attenuation in the tissue, like viscosity.

It will be appreciated that a system for determining a mechanical property by transient elastography, and in which the propagation of a periodic elastic wave is preliminary monitored to find homogeneous tissue, is a system that is somehow initially configured for transient elastography and further modified to implement the guiding technique presented above, which is very different, and even antagonistic from a transient elastography technique (which aims at separating compression waves and shear waves) and from prior art harmonic elastography techniques (which are focused on almost purely spatial features of the deformation field, and do not aim at helping the operator to properly position the probe).

In an embodiment according to the disclosed technology, the control module is programmed to determine, from at least some of the echo signals acquired in step b), data representative of a periodic deformation of the tissue, at different depths within the tissue and at different moments of the periodic mechanical vibration delivered to the tissue In an embodiment according to the disclosed technology, the homogeneity information comprises one of the following:
a graph representing the variation over depth of at least one temporal characteristic of the temporal, periodic variation of the deformation of the tissue; or
an indication specifying whether said characteristic varies with depth as if the tissue were homogeneous over a given range of depth, or not.

The graph may represent:
  the variation of the deformation over time, as a function of depth;
  a phase delay of the periodic deformation of the tissue, as a function of depth;
  an amplitude of an envelope of this periodic deformation, as a function of depth.

In an embodiment, the graph mentioned above represents the deformation of the tissue at different depths within the tissue and at different moments of the periodic mechanical vibration delivered to the tissue, the graph being a two-dimensional image whose pixels row index represents depth and whose pixels column index represents time, or conversely, each pixel having a pixel value representing the deformation of the tissue at the depth and time associated to the pixel considered.

In an embodiment, the indication mentioned above specifies whether a graph, which represents the deformation of the tissue at different depths within the tissue and at different moments of the periodic mechanical vibration delivered to the tissue, the graph being a two-dimensional image whose pixels row index represents depth and whose pixels column index represents time or conversely, each pixel having a pixel value representing the deformation of the tissue at the depth and time associated to the pixel considered, is comprised of diagonal stripes over said range of depth, or not.

In an embodiment the system comprises a manual adjustment control, such as a cursor, a slider, a button or a knob, that enables the operator to adjust manually the amplitude of the periodic mechanical vibration. This is useful in case the amplitude of the periodic deformation of the tissue, caused by the periodic mechanical vibration delivered to it, is too low or too high. The system may comprise an amplitude indicator for displaying to the operator information regarding the amplitude of the periodic deformation of the tissue.

In an embodiment the system is configured to automatically (that is without requiring an action of the operator) adjust the amplitude of the periodic mechanical vibration based on the amplitude of the resulting periodic deformation of the tissue. More precisely, the system may be configured to increase the amplitude of the periodic mechanical vibration when the amplitude of the resulting periodic deformation of the tissue is too low (lower than a given threshold), and to decrease the amplitude of the periodic mechanical vibration when the amplitude of the resulting periodic deformation of the tissue is too high (above another amplitude threshold).

In an embodiment the system is configured to adjust the amplitude of the transient mechanical pulse, delivered to the subject to measure a mechanical property of the tissue related to shear wave propagation by transient elastography, based on the amplitude chosen for the periodic mechanical vibration. In this case, the preliminary characterization of the tissue by periodic elastography enables, in addition to the different benefits presented above, to determine an amplitude of the transient mechanical pulse suitable to carry on the subsequent transient elastography measurement.

It will be appreciated that, according to the disclosed technology, the different embodiments presented above can be combined together, according to all technically possible combinations.

The disclosed technology provides also a method for characterizing tissue, carried on by means of a system comprising:
  a probe, to be hold against the skin of a subject and that comprises a vibrator to deliver mechanical vibrations to a tissue of a subject;
  an ultrasound emitter that is configured to emit a sequence of ultrasound shots and an ultrasound receiver that is configured to receive corresponding echo signals; and
  a control module programmed to make the system executing the following steps of the method:
    a) delivering a continuous and periodic mechanical vibration to the tissue of the subject, the periodic mechanical vibration comprising of a same vibration pattern repeated several times successively over time;
    b) emitting a sequence of ultrasound shots by means of the ultrasound emitter and acquiring corresponding echo signals received by the ultrasound receiver to track how the tissue is moved by the periodic mechanical vibration delivered to the tissue;
    c) providing homogeneity information to an operator of the system, the homogeneity information being determined from at least some of the echo signals acquired in step b), the homogeneity information being representative of the ability of the tissue to transmit elastic waves and of the homogeneity of the tissue with respect to the propagation of elastic waves;
  the control module being programmed so that steps b) and c) are executed by the system continuously, several times successively.

The features of the different embodiments of the system described above may apply also to this method for characterizing tissue.

BRIEF DESCRIPTION OF THE DRAWINGS

FIG. 5 shows a TM-mode graph acquired when the FIBROSCAN®'s probe is well positioned, with its axis centered on the organ to be characterized;

FIG. 6 shows different TM-mode graphs acquired when the probe is not properly positioned, its axis being close to an edge of the organ to be characterized, or in situations with liquid, air, or vessel interpositions that are not suitable for a proper mechanical characterization of the organ;

FIGS. 16 and 17 shows illustrative elastic wave propagation images, respectively from homogeneous and non-homogeneous tissue, in accordance with some embodiments of the disclosed technology;

DETAILED DESCRIPTION

Figure 7:
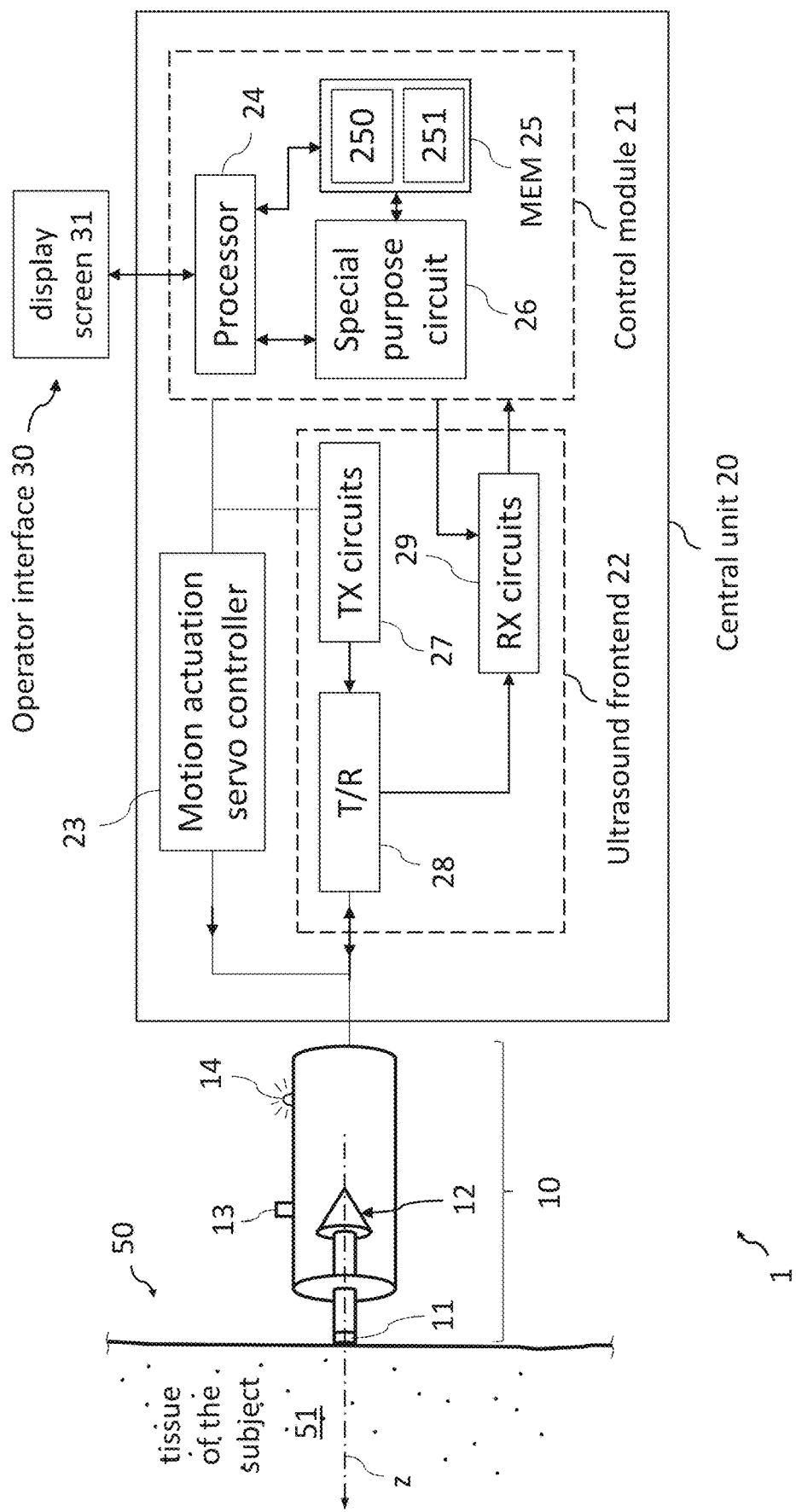
FIG. 7 is a block diagram of a system for characterizing tissue in accordance with some embodiments of the disclosed technology.

FIG. 7 is a block diagram of an ultrasound system 1 for characterizing tissue, configured for detecting homogeneous tissue. This system 1 comprises:
- a probe 10, to be hold against the body of a subject 50 and that comprises a vibrator 12 adapted to deliver mechanical vibrations to a tissue 51 of the subject;
- an ultrasound emitter that is configured to emit a sequence of ultrasound shots and an ultrasound receiver configured to receive corresponding echo signals, to track how the subject's tissue is moved by such mechanical vibrations;
- a control module 20 to control the probe 10 and to process data acquired by the ultrasound receiver.

The expression "tissue" is understood to mean a part of the body of the subject 50 (either a human or an animal). This expression does not necessarily designate a whole organ or a single organ. The tissue 51, to which mechanical vibrations are delivered and the deformation of which is tracked by the ultrasound shots, is a part of the subject's body located in the vicinity of the probe 20, along an axis z of the probe.

The system 1 is configured to determine a homogeneity information that indicates whether the tissue 51 is homogeneous and whether it can transmit elastic waves, in particular shear waves, or not, using a periodic elastography technique, and to provide this information to the operator by means of an operator interface 30.

The homogeneity information constitutes guiding information that helps the operator position and align the probe 20 with an organ to be characterized, such as liver or spleen. Once the probe 20 is adequately positioned thanks to this guiding information, one or several physical properties of the tissue can be determined to characterize this organ, for instance using transient elastography.

In this document, the expression "elastic wave" is understood to mean a low frequency mechanical wave or tissue deformation, that is to say a mechanical wave or tissue deformation whose central frequency is smaller than 500 hertz, or even smaller than 100 hertz, in contrast with ultrasound shots or echo signals, whose central frequency is typically higher than 0.1 megahertz or even higher than 1 megahertz (such ultrasound waves also create some kinds of elastic deformations, while propagating through the tissue, but at very high frequency, and they are not designated as "elastic waves", in this document).

To provide the homogeneity information, the control module 20 is more precisely programmed to make the system 1 for characterizing tissue executing the following steps:
a) delivering a continuous and periodic mechanical vibration PMV to the tissue 51 of the subject 50, the periodic mechanical vibration comprising of a same vibration pattern VP repeated several times successively over time (see FIG. 9, for instance);
b) emitting a sequence of ultrasound shots (like the sequence 80, 80', 80" of FIG. 9) by means of the ultrasound emitter 11 and acquiring corresponding echo signals received by the ultrasound receiver 11 to track how the tissue 51 is moved by the periodic mechanical vibration PMV delivered to the tissue;
c) providing the homogeneity information mentioned above to the operator 40 of the system, the homogeneity information being determined from at least some of the echo signals acquired in step b).

The control module 20 is programmed to execute steps b) and c) continuously (i.e. without interruption), repeatedly, until the operator 40 presses the control button 13 and triggers the transient elastography measurement. The homogeneity information provided to the operator 40 is thus continuously refreshed, which helps the operator find an adequate probe's position.

The system 1 may be configured to determine the homogeneity information mentioned above so that it indicates more precisely whether the tissue 51 is homogeneous over a given depth range or region of interest, or not. This depth range is for instance a depth range over which the subject's liver is expected to extend, should the probe 20 be adequately positioned. This depth range may for instance extend between a depth of 25 millimeters and a depth of 65 millimeters under the subject's skin (between which liver is typically located), or between a depth of 35 millimeters and a depth of 75 millimeters. This depth range delimits, within the tissue 51, a region of interest ROI of the tissue to be characterized (in FIG. 15, this region of interest extends between the two horizontal dashed lines).

The control module 20 is also programmed to determine at least one physical property of the tissue 51, so that the organ of interest can be characterized, once the probe 10 adequately positioned. This physical property may comprise:

an ultrasound parameter relative to ultrasound wave propagation within the tissue value, for instance an ultrasound attenuation value such as a BUA, a CAP and/or an attenuation measured at a particular frequency;

a mechanical property of the tissue related to shear wave propagation, determined by transient elastography, such as the propagation speed of shear waves $V_s$, the shear modulus of the tissue, the Young's modulus E of the tissue, or the tissue viscosity at low frequency (that is below 500 hertz).

More precisely, the system 1 of FIG. 7 can be configured to determine mechanical properties of tissues, related to shear wave propagation, for tissues that have a Young's modulus comprised between 1 and 100 kilopascals (which is suitable to study liver or spleen stiffness). The system 1 may also be configured to determine ultrasound attenuation values in tissues for which CAP values are comprised between 50 and 500 dB/m.

The structure of the system 1 of FIG. 7 is now be described in more detail. Then, a method for characterizing tissue in accordance with some embodiments of the disclosed technology, represented in FIG. 8 and that can be implemented by means of the system 1 of FIG. 7, will be presented, as well as exemplary results obtained by means of this system or method (see FIGS. 15 to 18).

As already specified, the probe 20 of the system 1 of FIG. 7 comprises a vibrator 12, such as an electromechanical vibrator or an acoustic speaker, to deliver mechanical vibrations to the tissue 51 of the subject. This mechanical vibration can be delivered to the tissue either as a force exerted upon the subject's body by a tip of the probe, as a displacement of a portion of the subject's body on contact with tip, enforced by the tip, or as a combination thereof.

In the system 1 of FIG. 7, the vibrator 12 is rotationally symmetrical around a vibrator axis, which coincide with the probe axis z. When the vibrator 12 vibrates, it induces displacements that are mainly longitudinal, parallel to its axis.

In the system 1 of FIG. 7, the ultrasound emitter and the ultrasound receiver are constituted by a same ultrasound transducer 11 (for instance a piezoelectric transducer). This ultrasound transducer 11 is rotationally symmetrical around a transducer axis and emits ultrasound beams centered on this axis. The transducer axis coincides with the vibrator's axis. The ultrasound transducer 11 has for instance a circular section, the vibrator's axis passing through the center of this section. In this system, the transducer 11 is part of the probe 10. It is mounted between the vibrator 12 and the tip of the probe. The tip of the probe is the part of the probe to be placed on contact with the subject's body. The tip is relatively small: its contact surface is typically smaller than 1 square centimeters. The tip may have a diameter smaller than 1 centimeter, or smaller than 8 or even 5 millimeters.

The probe 10 comprises a manual trigger, such as a control button 13 or dial. The system 1 is configured to achieve a transient elastography measurement when the manual trigger 13 is actuated.

The probe may comprise a manual adjustment control, such as a cursor, a slider, a button or a knob, to manually adjust the amplitude of the periodic mechanical vibration, the amplitude of the transient mechanical pulse, or both.

The system may be configured to automatically adjust the amplitude of the periodic mechanical vibration (in harmonic elastography) and/or the amplitude of the transient mechanical pulse (in transient elastography). The system may be configured to adjust automatically the amplitude of the transient mechanical pulse based on the amplitude of the periodic mechanical vibration previously adjusted.

It will be appreciated that, in other embodiments according to the disclosed technology, the ultrasound emitter and receiver could be constituted by two distinct transducers, instead of the same one. In addition, the probe may comprise an additional vibrator, like an electromechanical vibrator, an acoustic speaker or an electric motor provided with an eccentric cam. This additional vibrator may be rotationally symmetrical around the z axis, in the same manner as the vibrator 12 described above, or at least configured to induce vibrations parallel to the z axis. In such embodiments, the system could be configured to generate periodic mechanical vibrations by means of the additional vibrator, while generating transient mechanical vibrations by means of the vibrator 12.

The system 1 of FIG. 7 comprises also a central unit 20 including the control module 21, an ultrasound front end 22 with an ultrasonic transmitter module 27 and an ultrasonic receiver module 29, and a motion actuation servo controller 23 to control the vibrator 12. The ultrasound front end 22 and the motion actuation servo controller 23 are both connected to the control module 21 (that is to say that they can receive instructions from the control module 21 or send data to it).

The motion actuation servo controller 23 comprises an electric circuit configured to generate an electric signal appropriate to drive the vibrator 12, when instructed to by the control module 21. This electric circuit may comprise an electric current amplifier, or another type of amplifier.

The ultrasound front end 22 comprises, a switch 28 for alternatively transmitting and receiving ultrasonic signals. The ultrasonic transmitter module 27 of this front end 22 comprises an electric circuit configured to generate an electric ultrasonic signal appropriate to drive the ultrasound transducer 11 (such as the sequence of ultrasound shots described further below with reference to step b), when instructed to by the control module 21. This electric circuit may comprise an amplifier and a digital to analog converter (DAC), for instance an 8 to 16 bits DAC with a 10 to 1000 Mega-sample per second rate. The ultrasonic receiver module 29 comprises an electric circuit configured to acquire an electric ultrasonic signal (an echo signal), previously received by the ultrasound transducer 11 (and transmitted to ultrasonic receiver module 29 via the switch 28). The electric circuit of the ultrasonic receiver module 29 may comprise a tension amplifier, filters and an analog to digital converter (ADC), for instance an 8 to 16 bits ADC with a 10 to 1000 Mega-sample per second rate.

The control module 21 is a device or system comprising electric circuitry for processing data, such as a microprocessor coupled to a non-volatile memory comprising machine executable instructions and/or a programmable microcircuit like an FPGA (field programmable gate array) or a DSP (digital signal processor).

As represented in FIG. 7, the control module 21 comprises more specifically:
a processor 24, for instance a general purpose processor;
a signal processing circuit 26, for instance an FPGA (FPGA coprocessor), a DSP or another programmable circuit; and
a physical non-transitory memory module 25, comprising a non-volatile memory 250 for storing machine executable instructions to be executed by the processor 24, and, optionaly, a RAM memory 251 for storing signal data and instructions during the system operation.

The control module 21 can be in the form of an FPGA carrier board, for instance. The processor 24 can be either embedded within the signal processing circuit 26 (e.g. within the FPGA), or off this circuit (e.g.: off the FPGA, the FPGA then executing special signal processing tasks, like echo signals correlation calculations, to offload the processor 24). The signal processing circuit 26 is configured to process the echo signal received by the transducer (once digitized by the ultrasonic receiver module 29).

As already mentioned, the control module 21 is programmed to make the system 1 executing the steps a), b) and c) presented above. The control module 21 is programmed to make the system execute these steps in that it contains instructions, which, when executed by the control module 21, make the control module 21 to:
control the motion actuation servo control 23 so that it drives the vibrator 12 to deliver the periodic mechanical vibration to the tissue (step a));
control the ultrasound front end 22 so that it drives the ultrasound transducer 11 which in return emits a sequence of ultrasound shots to track how the tissue is moved by the periodic mechanical vibration, and so that the ultrasonic receiver module 29 acquires corresponding echo signals (step b));
determine, from at least some of the echo signals thus acquired, homogeneity information representative of the ability of the tissue to transmit elastic waves, that is to say to let elastic waves propagate through it, and of the homogeneity of the tissue with respect to the propagation of elastic waves, and providing this information to the operator, for instance by transmitting it to the operator interface 30 (step c)).

The instructions, whose execution make the control module 21 to control the system 1 so that it executes any given step, in particular steps a), b) and c), are stored in the non-volatile memory 250, in the form of machine executable instructions or code instructions, or physically embedded in the programmable circuit 26, in the form of electric (reconfigurable) connections between gates of this circuit, or a combination thereof.

The control module 21 may be more specifically programmed in order to, in step c):
c0) determine, from the echo signals acquired in step b), data representative of a deformation of the tissue 51, at different depths d within the tissue and at different moments t1, t2, t3 of the periodic mechanical vibration delivered to the tissue; and to
c1) determine the homogeneity information from the data representative of the deformation of the tissue 51 determined in step c0).

Step c0) can be executed using a correlation technique or another patterning matching algorithm, to determine how portions of the tissue 51 move under the influence of the elastic wave that is passing through it (the elastic wave being generated by the periodic mechanical vibration delivered by the system). For example, the tissue in a small zone of the region of interest may move slightly away from the transducer 11 and then slightly toward the transducer 11 as a spatial period of the elastic wave passes through this zone. Step c0) is typically executed by the programmable circuit 26, to offload the processor 24.

Figure 8:
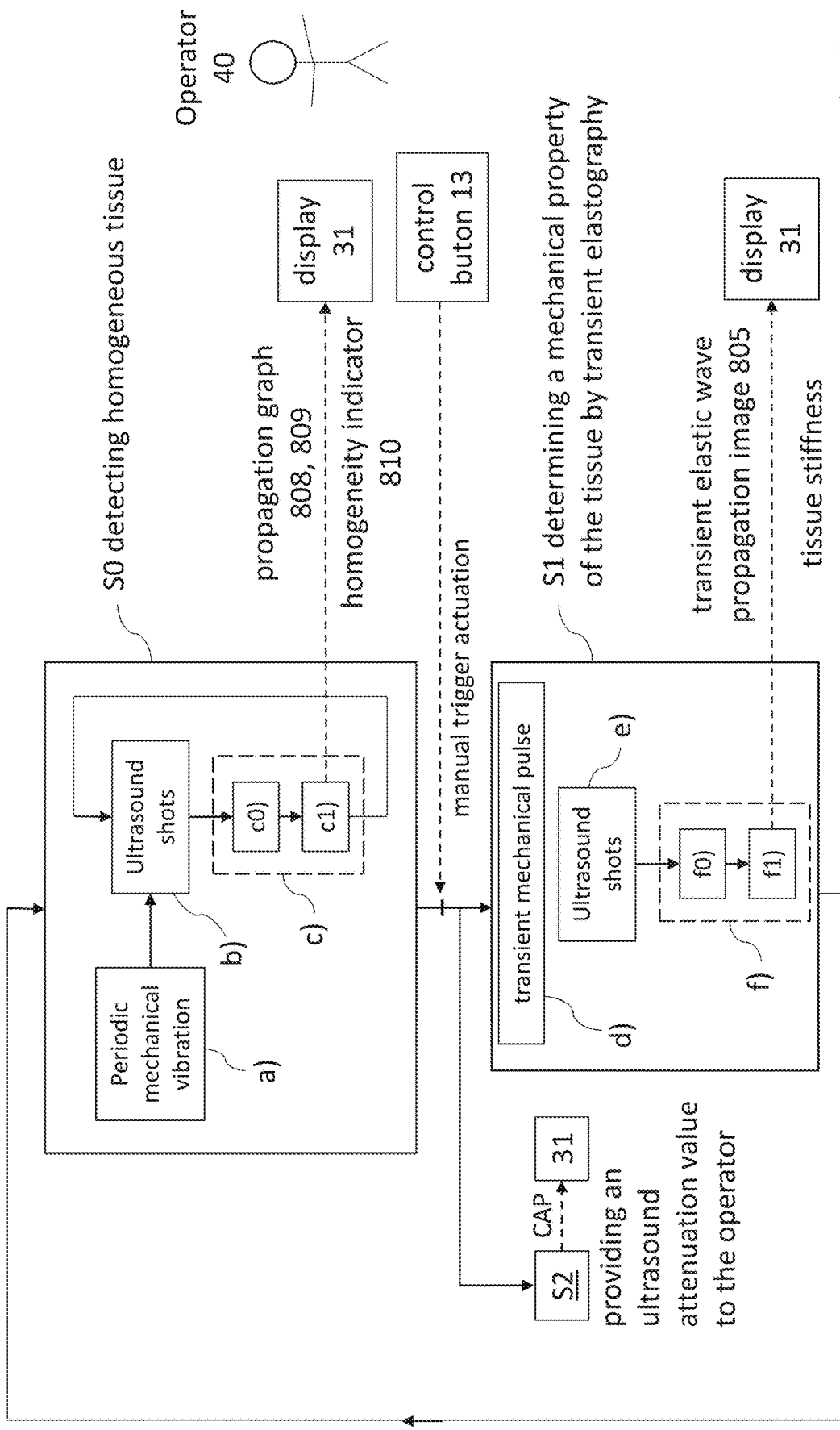
FIG. 8 is flow chart of a method for characterizing tissue in accordance with some embodiments of the disclosed technology.

The control module 21 may be further programmed to, inter alia, make the system 1 execute the different steps of the method for characterizing tissue represented in FIG. 8.

As represented in FIG. 7, the system 1 for characterizing tissue comprises the operator interface 30 mentioned above. Still, in other embodiments according to the disclosed technology, the operator interface could be distinct from the system for characterizing tissue. The operator interface may for instance be embedded in a smartphone or a computer communicating with the system for characterizing tissue. In such a case, to provide the homogeneity information to the operator, the control module 21 transmits this information to the external operator interface by means of a communication module of the system for characterizing tissue. The communication module may be an electric circuit configured to exchange data using a wire or wireless link, for instance according to an USB, a Firewire, a Bluetooth, a 6LoWPAN, a ZigBee, a Z-Wave, or a Sigfox protocol.

Figure 15:
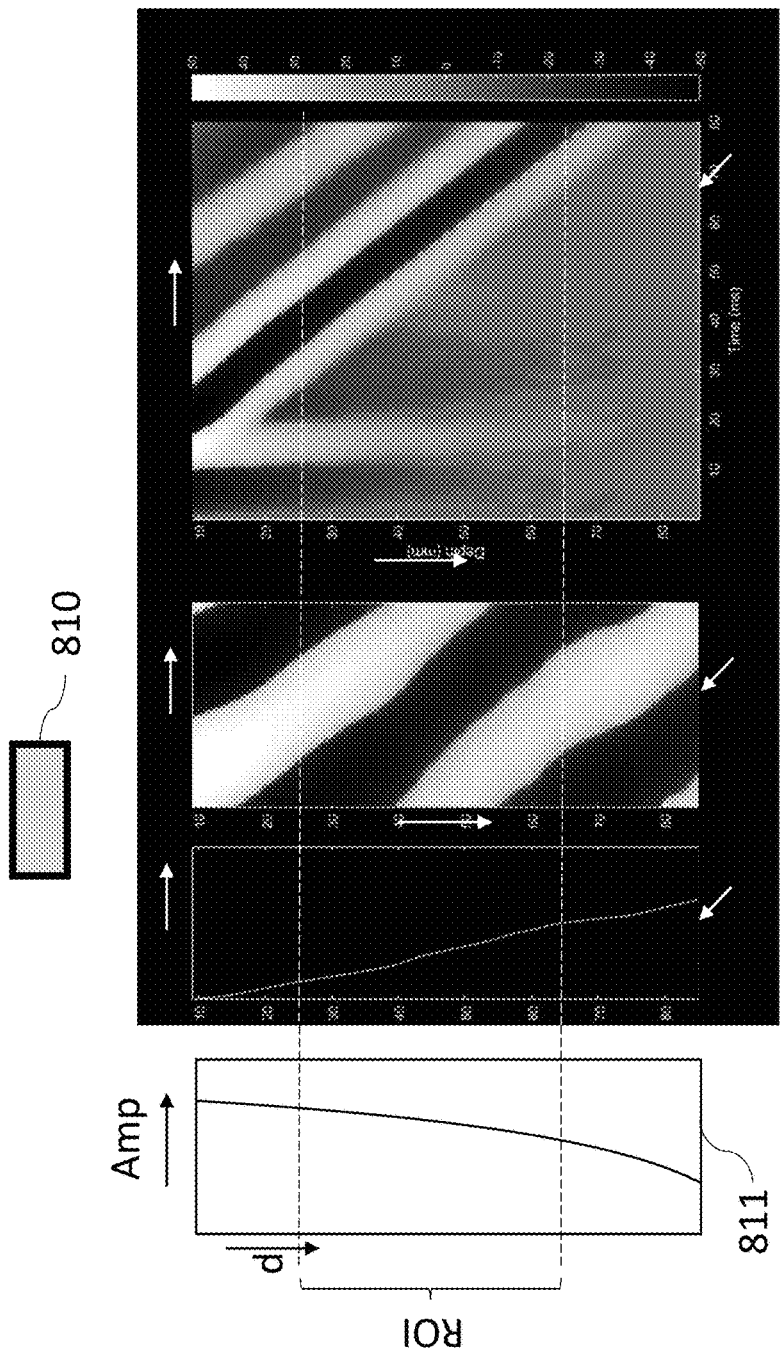
FIG. 15 shows different graphs and an indicator, displayed to an operator by a system for characterizing tissue in accordance with some embodiments of the disclosed technology.

With the system of FIG. 7, the homogeneity information determined by the control module 21 is provided to the operator by means of the display screen 31 of the operator interface 30, for instance in the form of the graphs 808, 809 and indicator 810 of FIG. 15. The operator interface 30 may comprise also a light emitting diode or other light emitting device 14, arranged on the probe 10, for visually indicating to the operator 40 whether the tissue is homogeneous or not by means of a change of color or luminous intensity of the light emitted.

In some embodiments, according to which the system is a pocket system, the operator interface comprises the light emitting device mentioned above, but no display screen.

Still in another embodiment, the operator interface comprises a speaker for indicating to the operator whether the tissue is homogeneous or not by means of an audible signal. Such homogeneity information could also be provided to the operator by means of a haptic indication such as a change of type or amplitude of the mechanical vibration.

Though the central unit 20 and the probe 10 are represented as separate parts in FIG. 7, all or part of the modules 21, 22, 23 of the central unit 20 presented above could be arranged within the probe.

It will be appreciated that a number of variations may be made in the system for characterizing tissue presented above without departing from the scope of the disclosed technology. For instance, some electric functionalities could be distributed differently within the central unit than what has been described above. As an example, the DAC and ADC could be located in the control unit instead of the ultrasonic transmitter and receiver modules. Some of the modules 23 to 29 could be merged together, or distributed. Moreover, the control unit may comprise just one processor, instead of one processor and a signal processing unit. Alternatively, the control unit may comprise a greater number of processing units than in FIG. 7.

A flow chart of a method for characterizing tissue in accordance with some embodiments of the disclosed technology is represented in FIG. 8. As already mentioned, the control module 21 of the system 1 of FIG. 7 can be programmed to make the system 1 to execute this method.

This method comprises the following main steps: S0, detecting homogeneous tissue, S1, measuring tissue stiffness by transient elastography, and S2, providing an ultrasound attenuation value to the operator. In step S0, the system 1 delivers the continuous periodic mechanical vibration to the subject to test tissue homogeneity and provides the homogeneity information mentioned above to the operator 40. This information is continuously refreshed, so that the operator can monitor in real time the tissue homogeneity to test different probe's positions. Once the homogeneity information indicates that the tissue 51 under examination is homogeneous, the operator 40 actuates the manual trigger (e.g.: the operator presses the control button 13). The execution of step S0 then stops and the execution of steps S1 and S2 starts. Once the tissue stiffness measurement has been made in step S1, the execution of step S0 restarts so that the operator can be assured that the probe is still placed in front of homogenous tissue. The process of alternating between the emission of the continuous periodic mechanical vibration (for homogeneity assessment) and the measurement of tissue stiffness by transient elastography can continue until a required number of tissue stiffness measurements have been obtained.

Steps So, S1 and S2 are now described in more detail, one after the other.

Step S0: Detecting Homogeneous Tissue

As represented in FIG. 8, step So comprises steps a), b) and c) presented above. Step So starts with step a), during which the control module 21 controls the vibrator 12 (via the motion actuation servo control 23) so that the vibrator 12 delivers a continuous and periodic mechanical vibration PMV to the tissue 51 of the subject 50. This periodic mechanical vibration PMV is continuously delivered all along step S0 (it lasts all along step S0). Once the emission of this periodic mechanical vibration PMV has begun, the control module executes step b), during which the control module controls the ultrasound transducer 11 (via the ultrasonic transmitter module 27) so that it emits a sequence of ultrasound shots to track how the tissue is moved by the periodic mechanical vibration, and acquires corresponding echo signals (via the ultrasonic receiver module 29). Then, in step c), the control module determines the homogeneity information from the echo signals acquired in step b) and then provides it to the operator. Then, the control module executes again steps b) and c), while the periodic mechanical vibration PMV continues to be delivered, to provide new, updated homogeneity information to the operator. The set of steps comprising step b) and c) is thus continuously executed, several times successively, until step S0 is stopped by the operator actuating the manual trigger mentioned above. For example, in the case of FIG. 9, the set of steps comprising step b) and c) is repeated every 50 milliseconds (with a repetition rate of 20 hertz). So, in this case, if it takes 3 seconds for the operator to find a proper probe location and to actuate the manual trigger (for example), then step So will last for approximately 3 seconds and the set of steps comprising step b) and c) will be repeated approximately 60 times.

In the embodiments of FIG. 8, the set of steps comprising step b) and c) is executed in real-time, that is to say with a repetition rate higher than or equal to 10 hertz, or even higher than or equal to 20 hertz, and with a lag time smaller than or equal to 1 second, or even smaller than or equal to 0.1 second, or smaller than 0.03 seconds. The lag time is the time interval between the beginning of the emission of the sequence of ultrasound shots, in step b), and the instant at which the updated homogeneity information, determined from the echo signals acquired in step b), is provided to the operator.

In the method of FIG. 8, step c) comprises the sub-steps c0) and c1) described above. In step c0), the control module determines, from the echo signals acquired in step b), data representative of a deformation of the tissue 51, at different depths d within the tissue and at different moments t1, t2, t3 of the periodic mechanical vibration delivered to the tissue. In step c1), the homogeneity information provided to the operator comprises a graph representing, both as a function of time t and as a function of depth d, the deformation of tissue caused by the periodic mechanical vibration (this deformation has been determined in step c0)), like graphs 808 of FIGS. 9 and 15, graphs 168 and 178 of FIGS. 16 and 17, or graphs 188a to 188e of FIG. 18.

Steps a), b) and c) are now described in more detail.

Figure 9:
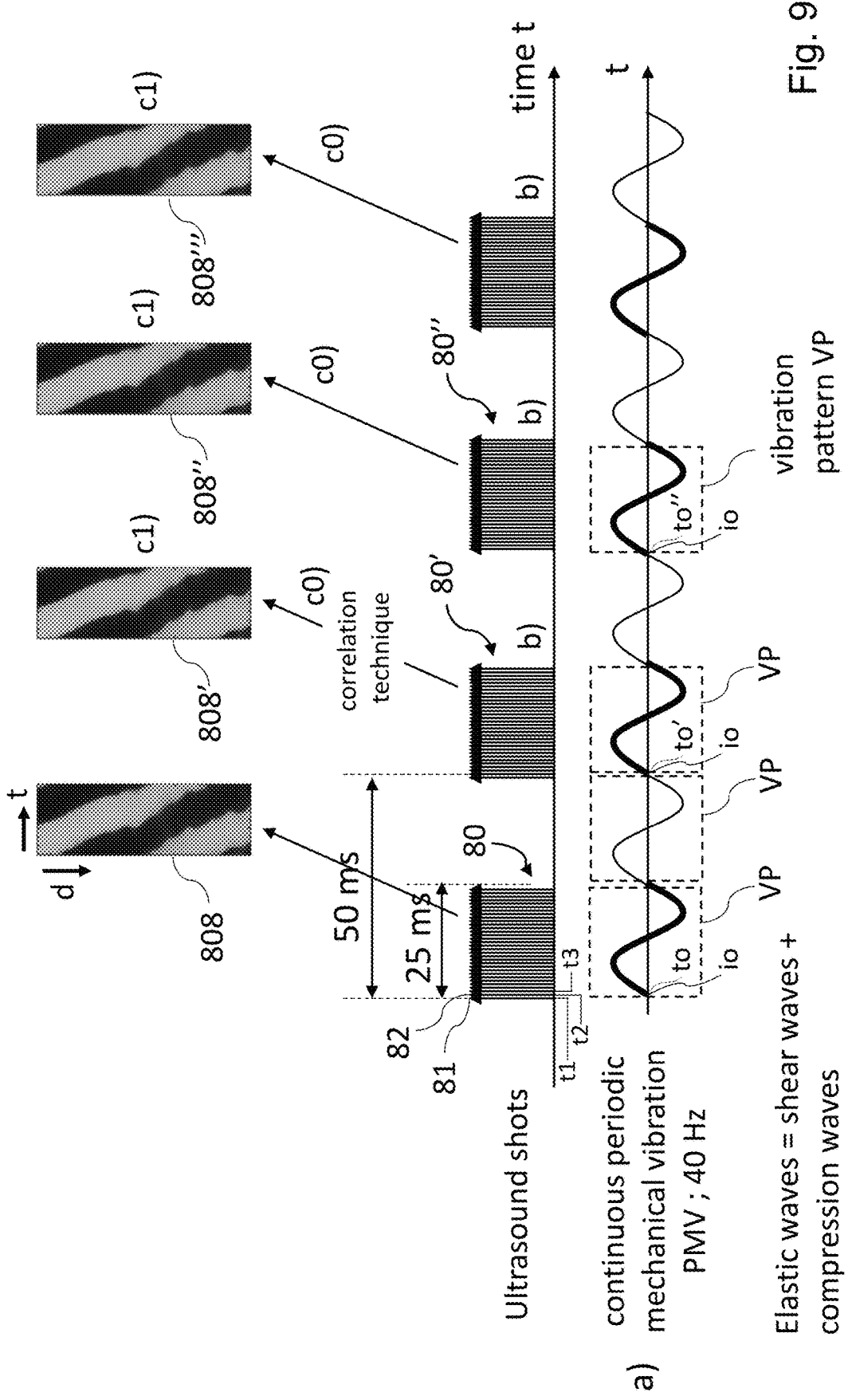
FIG. 9 shows a continuous and periodic mechanical vibration delivered to a tissue of a subject, sequences of ultrasound shots emitted to track a deformation of the tissue caused by this vibration and elastic wave propagation images obtained thereof, according to some embodiments of the disclosed technology.
Figure 10:
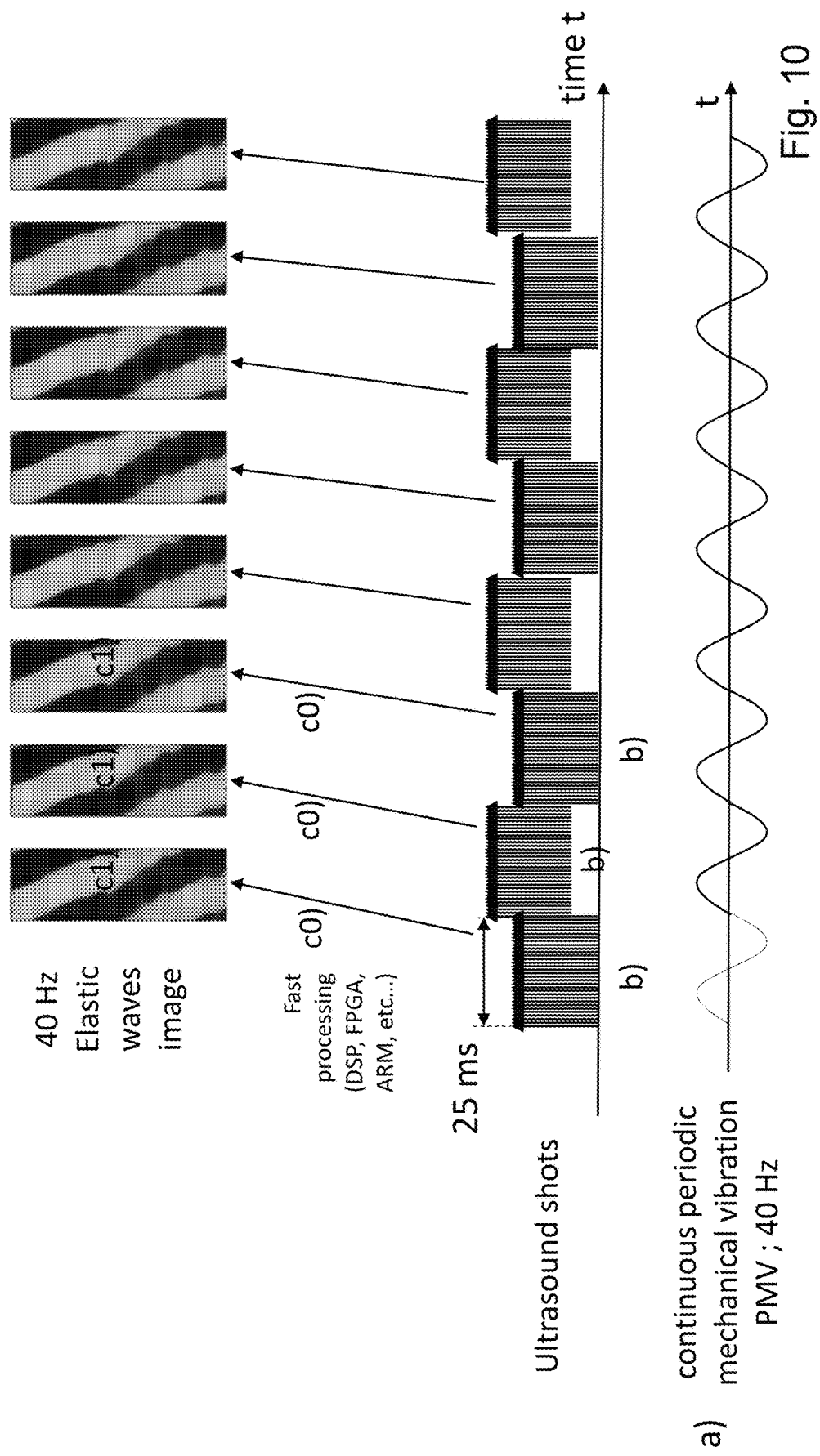
FIG. 10 shows a continuous and periodic mechanical vibration delivered to a tissue of a subject, and another way to emit sequences of ultrasound shots to track a deformation of the tissue caused by this vibration, according to some embodiments of the disclosed technology.
Figure 11:
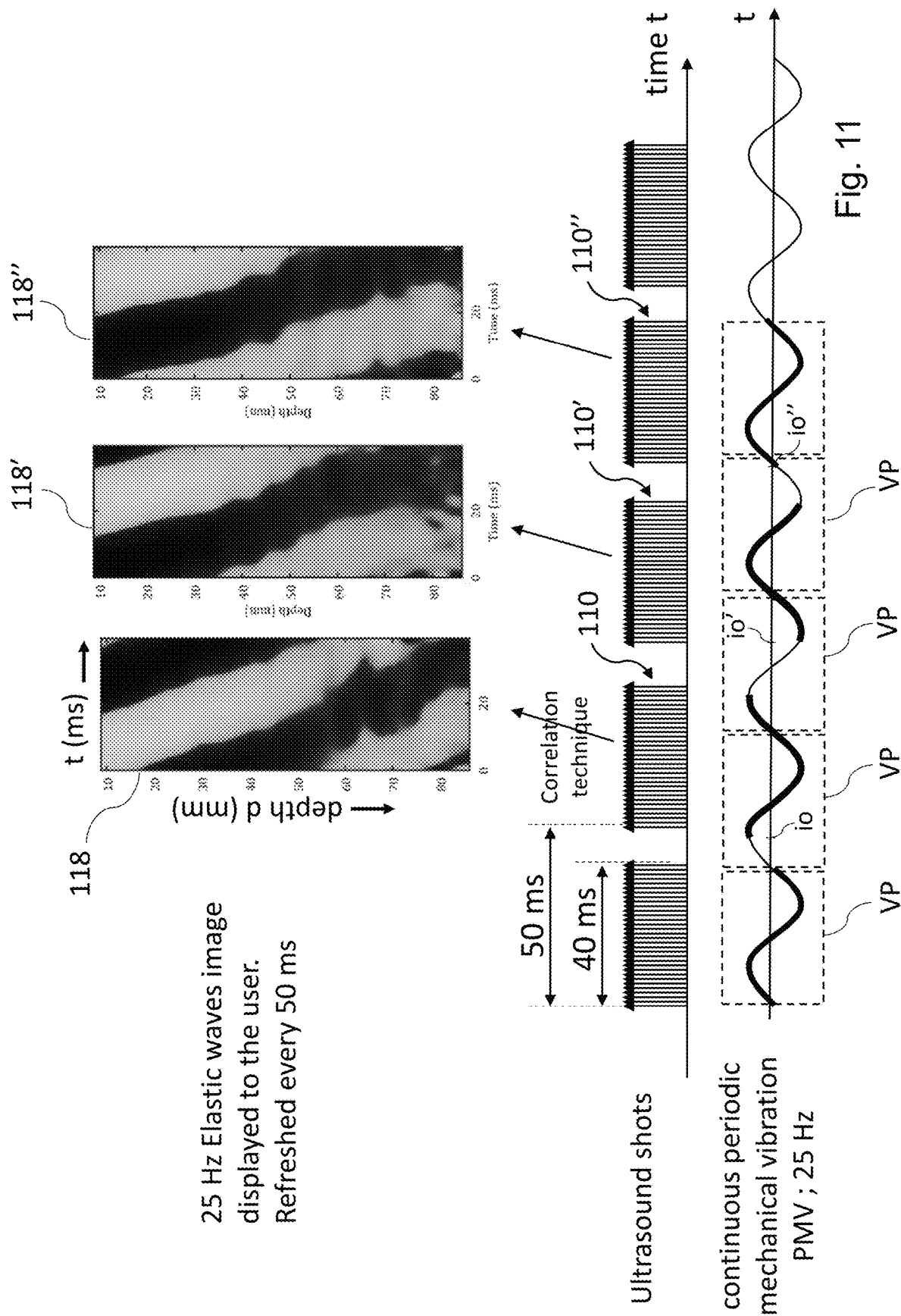
FIG. 11 shows a continuous and periodic mechanical vibration delivered to a tissue of a subject, still another way to emit sequences of ultrasound shots to track a deformation of the tissue caused by this vibration and periodic elastic wave propagation images obtained thereof, according to some embodiments of the disclosed technology.

In step a), the periodic mechanical vibration delivered to the tissue has a base frequency, that is to say a fundamental frequency, comprised between 10 hertz and 200 hertz. It may have a base frequency comprised more specifically between 10 hertz and 60 hertz. Such frequency values are favorable for a deep penetration of the vibration within the tissue, while still fast enough to determine updated homogeneity information with a refresh rate higher than or equal to 10 hertz, thus enabling real-time monitoring of the tissue homogeneity. The periodic mechanical vibration PMV may for instance have a base frequency of 40 hertz (and thus a period of 25 milliseconds), like in FIGS. 9 and 10, or of 25 hertz (and thus a period of 40 milliseconds), like in FIG. 11. As represented in FIGS. 9, 10 and 11, the periodic mechanical vibration PMV is a sinusoidal vibration. Still, other periodic waveforms, such as triangular waveforms, could be employed. The periodic mechanical vibration PMV is continuous in that it comprises a same vibration pattern VP (here a sine wave period) repeated several times successively over time, cyclically, one immediately after the other. Each new instance of the vibration pattern starts immediately after the previous one, with no delay in between. The vibration pattern is repeated with a repetition rate that is the base frequency mentioned above. As already mentioned, the periodic mechanical vibration lasts continuously all along step S0. So, the periodic mechanical vibration lasts typically 1 second or more. The part of the subject's tissue 51 in contact with the probe 20 oscillates with an amplitude comprised typically between 0.1 and 2 millimeters, as a result of the periodic mechanical vibration delivered by the probe.

In step b), the control module 21 instructs the ultrasonic transmitter module 27 to generate a sequence of ultrasound electric pulses that are converted by the ultrasound transducer 11 which, in return, emits a sequence of short ultrasound pulses, named ultrasound shots, to track, or in other words to probe, how the tissue 51 is moved by the periodic mechanical vibration PMV. FIG. 9 shows a representative sequence 80 of ultrasound shots 81, 82, . . . . The central frequency of each ultrasound shot is comprised for instance between 1 and 5 megahertz. The duration of each shot, for instance equal to 100 microseconds, is typically smaller than a millisecond. In step b), the control module 20 also acquires a sequence of corresponding echo signals, received by the ultrasound transducer 11. Each echo signal is corresponding to an ultrasound shot emitted by the transducer in that the echo signal is an ultrasound wave back scattered by the tissue in response to the emission of the ultrasound shot considered (or at least is representative of this back scattered wave). Each echo signal is representative of back scattering properties of the tissue, as a function of the depth d within the tissue (as each instant, within one of these short echo signals, corresponds to a given depth in the tissue, since the round-trip travel time of an ultrasound wave between the transducer and a point located at the depth considered depends directly on that depth).

As already mentioned, these successive echo signals are acquired to be compared one with each other, for instance using a correlation technique or another patterning matching algorithm, to determine how portions of the tissue 51 move under the influence of the elastic wave that is passing through the tissue (this determination is carried on in step c)). Thus, to prevent decorrelation between two echo signals successively acquired, the ultrasound shots are emitted with a pulse repetition rate higher than or equal to 500 Hertz, or even higher than or equal to 1 kilohertz, in step b) (indeed, such decorrelation could occur, due to global tissue displacements caused by respiration, for instance, when the duration between the two successive shots is too long). Typically, the pulse repetition rate is comprised between 1 kilohertz and 10 kilohertz (depending on the control module calculation capacities). So, within the sequence of ultrasound shots emitted in step b), the duration between any shot, and the shot immediately following it, is smaller or equal to 2 milliseconds, or even smaller to or equal to 1 millisecond.

In the method of FIG. 8, the sequence of ultrasound shots emitted in step b) spans at least over one half, or even over at least three fourth of a same period of the periodic mechanical vibration PMV delivered to the tissue (for instance over a whole period of the periodic mechanical vibration). And this sequence comprises at least 10, or even 50 ultrasound shots per period of the periodic mechanical vibration. As a result, in this case, a same period, or at least the major part of a same period of the periodic mechanical vibration PMV is sampled, all at once, as a whole, by the sequence of shots emitted in step b). As already explained, this enables a much better monitoring of the propagation of the periodic elastic deformation than with stroboscopic like sampling methods.

In step b), the control module may in particular control the ultrasonic transmitter module 27 so that it generates the sequence of ultrasound shots as represented in FIG. 9, 10 or 11.

In the examples of FIGS. 9 and 10, the sequence 80 of ultrasound shots emitted in step b) spans more precisely over one period of the periodic mechanical vibration PMV. In these examples, the ultrasound shots repetition rate is equal to 2 kilohertz. Therefore, the sequence of ultrasound shots comprises 50 shots per period of the periodic mechanical vibration (the frequency of the periodic mechanical vibration being equal to 40 hertz, in these examples).

In the example of FIG. 11, the sequence of ultrasound shots emitted in step b) spans over more than a period. The ultrasound shots repetition rate may also be equal to 2 kilohertz, corresponding to 80 shots per period (the frequency of the periodic mechanical vibration being equal to 25 hertz, in this case).

The sequence of ultrasound shots 80, 80', 80" emitted in step b) could be emitted in a synchronized manner with respect to the periodic mechanical vibration, starting from an instant io which, within a cycle of the periodic mechanical vibration PMV delivered to the tissue 51, is the same for each execution of step b). As shown in FIG. 9, this enable to obtain a stable propagation graph 808n with no rolling (time shifting) effect from one execution of steps b) and c) to the other.

In such a case, the absolute time to, to', to" at which the sequence of ultrasound shots starts is different from one execution of step b) to the other. But the time at which the sequence starts relative to the beginning of the cycle of the periodic mechanical vibration is the same for each execution of step b) (more precisely, the time at which the sequence starts, relative to the beginning of the cycle of the periodic mechanical vibration that is the closest to this starting time—that is to say relative to the beginning of the instance of the vibration pattern that is the closest to this starting time—is the same for each execution of step b)).

In the case of FIGS. 9 and 10, for instance, for each execution of step b), the sequence of ultrasound shots starts almost at the beginning of a period of the periodic mechanical vibration, when the vibration passes through zero while increasing (the sequence of ultrasound shots could also start a given, fixed delay time after the beginning of a period of the periodic mechanical vibration).

Thanks to this synchronization, the propagation graph representing the deformation of the tissue (that is deduced from the shots emitted in step b)) both as a function of depth and as a function of time, starts, for each new execution of steps b) and c), from the same instant io within a cycle of the periodic mechanical vibration (like the different propagation graphs 808, 808', 808" of FIG. 9, displayed successively to the operator). This graph thus remains stable from one execution to the other, is aligned temporally, instead of rolling. Thanks to this stabilization, the graph is easier to understand for the operator (as the deformation monitoring is not disturbed by temporal rolling, shifting of the graph). The operator can thus determine more easily whether the probe is placed in front of a homogeneous tissue, in a situation adequate to measure a physical parameter of the tissue, or not.

Step b) can be repeated with a rate such that each new sequence of ultrasound shots is emitted immediately after the other, with no interruptions between them, like in FIG. 10. In the example of FIG. 10, a sequence of ultrasound shots is thus emitted (to track the tissue deformation) for each period of the periodic mechanical vibration PMV. Step b) can also be repeated with a slower rate, for instance by emitting a sequence of ultrasound shots every two periods of the periodic mechanical vibration PMV, like in the case of FIG. 9, when the control module 21 has a more limited processing speed. In the case of FIG. 9, a new, updated version of the homogeneity information is provided to the operator after each emission of the sequence of ultrasound shots, before the next sequence of ultrasound shots is emitted. In other words, in this case, the execution of step c) is completed before a new execution of step b).

In step b), the sequence of ultrasound shots 110, 110', 110" could also start from instants io, io', io" which, within a cycle of the periodic mechanical vibration PMV delivered to the tissue 51, are different from one execution of step b) to the other, as represented in FIG. 11. In this such a case, if a raw propagation graph like graph 118, 118 or 118" of FIG. 11 were provided to the operator, in step c), the operator would perceive the disturbing rolling, time shifting effect mentioned above when this raw graph would be refreshed (a "raw propagation graph" is understood to mean a graph showing the tissue deformation both as a function of time and depth, the deformation being displayed over time in the order it was sampled; in other words, in such a raw graph, the temporal coordinate is the actual time at which the deformation was measured).

Figure 12:
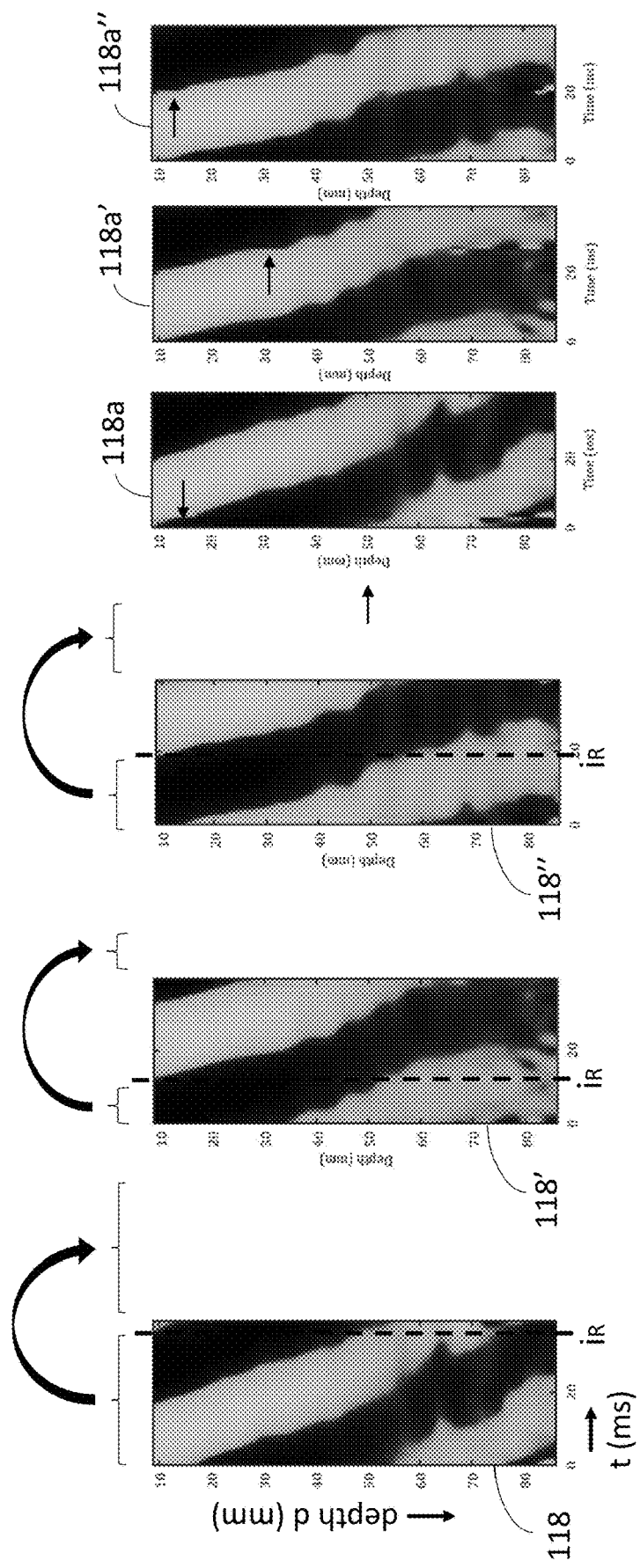
FIG. 12 shows how the periodic elastic wave propagation images of FIG. 11 can be temporarily aligned for operator viewing in accordance with some embodiments of the disclosed technology.
Figure 13:
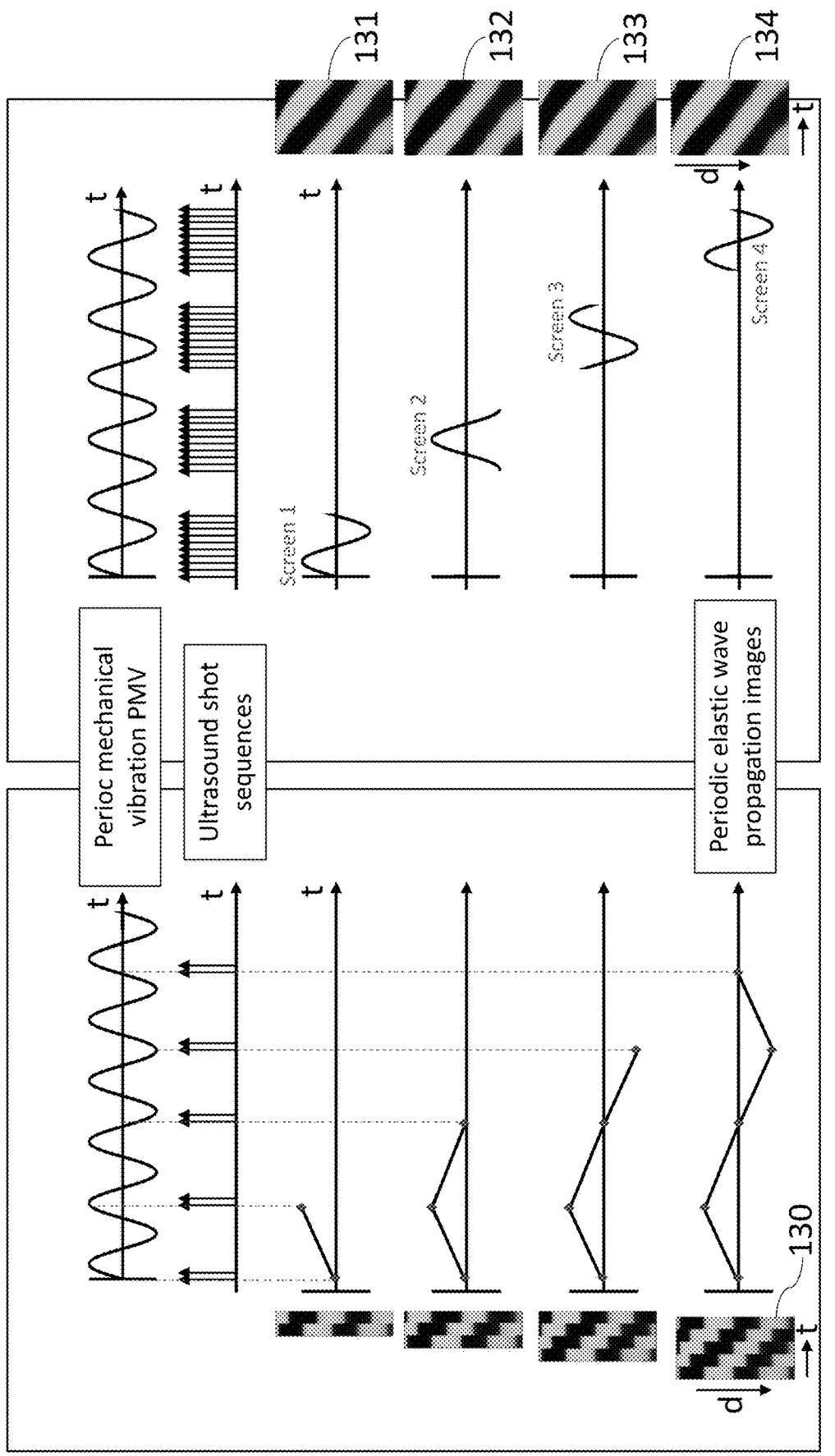
FIG. 13 illustrates differences between a low sampling rate, stroboscopic like method for tracking a periodic deformation of a tissue, and a high sampling rate method for tracking such a periodic deformation of a tissue, in which a same period of the deformation of the tissue is monitored all at once, as a whole, in accordance with some embodiments of the disclosed technology.

So, in this case, to prevent such a rolling effect, the deformation data determined from the echo signals is post-processed (in step c)) in order to be re-aligned temporally before being displayed, in the form of re-aligned propagation graphs that start all from a same, fixed instant, within a cycle of the periodic mechanical vibration, like graphs 118a, 118*a'*, 118*a"* of FIG. 12. In other words, the re-aligned propagation graph provided to the operator in step c) starts from a reference instant iR which, within a period of the periodic mechanical vibration delivered to the tissue, is the same each time the graph is updated on the base of newly determined deformation data. The temporal re-alignment can be achieved as follow: the deformation data obtained for times (actual, absolute measurement times) that precede the reference instant iR are moved as a block to be placed at the end of the deformation data, from a temporal point of view (as if they had been measured just after the end of the sequence of ultrasound shots), as represented schematically in FIG. 12. The reference instant iR is a given, fixed moment within the vibration pattern VP that is repeated several times successively, for instance the beginning of this vibration pattern, when the vibration passes through zero while increasing. This re-aligning technique stabilizes well the display of the propagation graph, from a temporal point of view. Though, the re-aligned propagation graph obtained in this way comprises a discontinuity, at the junction with the cut-and-paste block of data that has been temporally shifted (this discontinuity is identified by an arrow, in the graphs 118*a*, 118*a'*, 118*a"* of FIG. 12). It will be appreciated that propagation graphs obtained by directly synchronizing the emission of the sequence of ultrasound shots with the periodic mechanical vibration, as in FIGS. 9 and 10, do not comprise such discontinuities.

Step c).

As already mentioned, in step c0), the control module 21 determines deformation data representative of the deformation of the tissue, for different depths within the tissue and at different moments of the periodic mechanical vibration delivered to the tissue, by comparing successive ultrasound echo signals using a correlation technique or another patterning matching algorithm.

The term deformation is considered in a broad sense in this document. It encompasses any movement parameter such as the displacement, the speed, the deformation, the deformation rate, the speed of deformation and any mathematical transformation applied to these parameters.

In step c1), the homogeneity information is determined from the deformation data determined in step c0). The homogeneity information may comprise one of the followings:
a propagation graph, like the ones 808, 168, 178, . . . presented above;
a graph representing a phase delay $\varphi$ of the periodic deformation of the tissue, as a function of depth d, like graph 809 of FIG. 15;
a graph representing an amplitude Amp of an envelope of the periodic deformation of the tissue, as a function of depth d, like graph 811 of FIG. 15;
an homogeneity indicator 810.

FIG. 15 shows an example of the elements that can be displayed to the operator by means of the operator interface screen 31, to provide him/her with the homogeneity information. In the case of FIG. 15, the homogeneity information comprises all the elements listed above. Still, in other embodiments, the homogeneity information could comprise just one, or just some of these elements. These different elements, and the way to determine them, are now described in more detail.

The propagation graph, that represents the deformation of the tissue at different depths within the tissue and at different moments of the periodic mechanical vibration can be a two-dimensional image 808 compounded by the control module 21, whose pixels row index represents depth d and whose pixels column index represents time t (or conversely), each pixel having a pixel value representing the deformation of the tissue at the depth and time associated to the pixel considered. The pixel value, that represents the deformation value at the point and instant considered, can be a luminosity value, like in FIG. 15 (the pixel luminosity being all the higher than the algebraic deformation value is high), or a color value (like a hue value), or a combination thereof.

As already mentioned, when the tissue is homogeneous and suitable for elastic wave propagation (no air or liquid interposition), such a periodic elastic wave propagation image 808 is comprised of one or more diagonal stripes. These stripes are diagonal in that they are slanted, in the t-d coordinate system. Their inclination is due to the propagation time of the periodic elastic wave, from the skin of the subject to the depth considered. The slope of these stripes is thus somehow representative of the speed at which these elastic waves propagate in the tissue.

Figure 18:
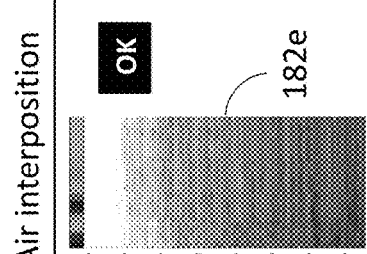
FIG. 18 shows illustrative TM-graphs, periodic elastic wave propagation images and transient elastic wave propagation images, provided to the operator in accordance with some embodiments of the disclosed technology, these graphs and images being obtained in a number of different situations and probe positions.

As explained in detail above with reference to FIGS. 16 to 18 (see the section presenting the summary of the disclosed technology), such propagation graphs enable the operator to readily determine whether the tissue is homogeneous and suitable for elastic wave propagation or not.

When the tissue 51 is homogeneous and suitable for elastic wave propagation (for example there is no air or liquid interposition between the probe and the targeted tissue), the phase delay $\varphi$ varies substantially linearly over depth, as shown by the graph 809 of FIG. 15.

Figure 14:
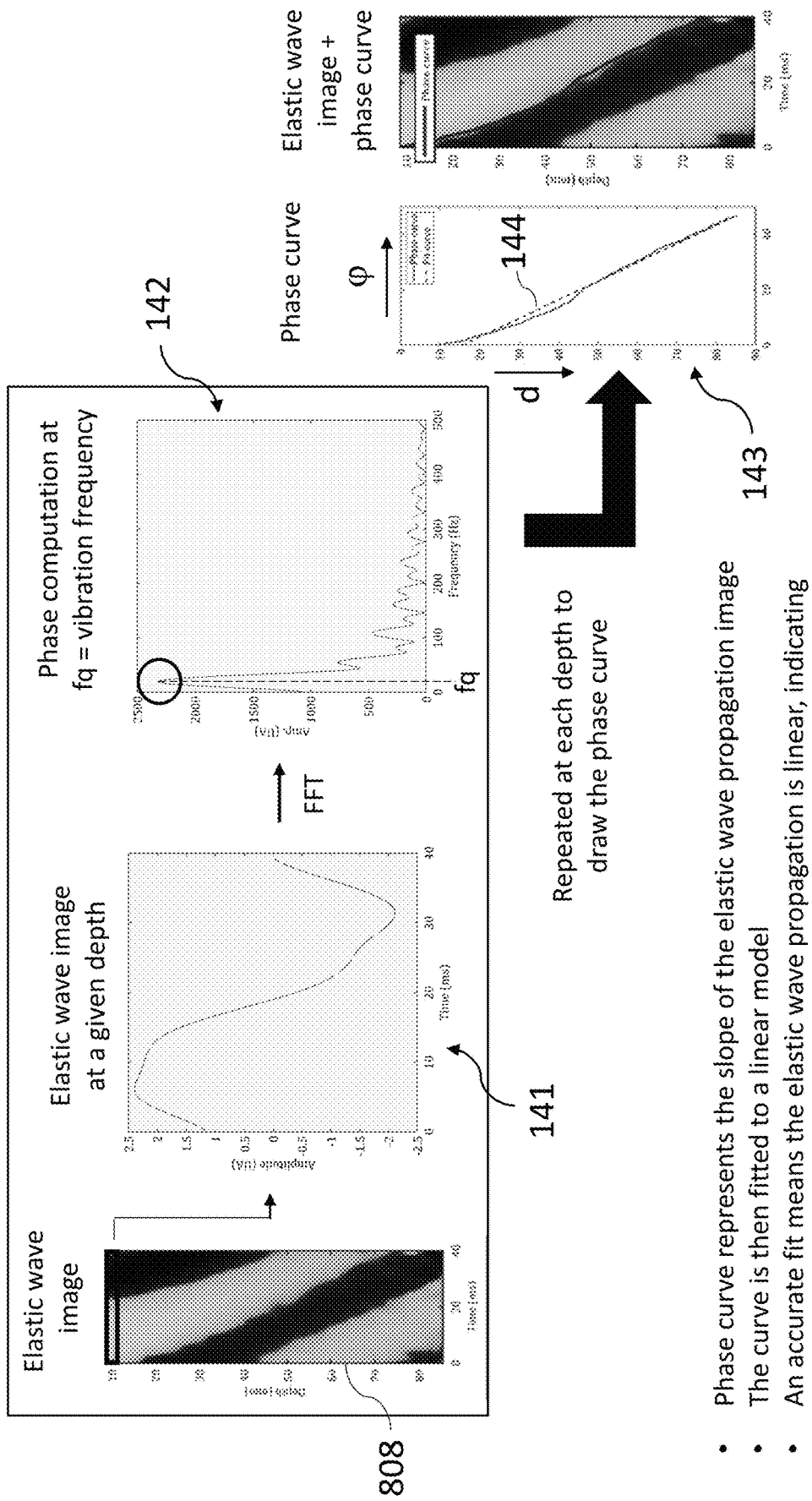
FIG. 14 shows a phase delay of an elastic wave at a particular depth in the tissue is determined in accordance with some embodiments of the disclosed technology.

The phase delay $\varphi$ can be expressed as a duration or as an angle (in degrees or radians). At a given depth d, the phase delay $\varphi$ represents the dephasing between the periodic deformation of the tissue at that depth, and a reference periodic oscillation, such as the periodic mechanical vibration delivered to the tissue, or the periodic deformation of the tissue in an upper portion of the tissue. The control module 21 may be programmed to determine the phase delay $\varphi$ from a frequency-domain representation of the deformation data, as represented in FIG. 14. In such a case, the measurement of the deformation of the tissue over time 141, at a particular depth, is transformed into a frequency-domain representation of this variation 142, (using a Fourier transform or other time domain to frequency domain conversion). This frequency-domain representation shows a peak at a frequency fq that is the base frequency of the periodic mechanical vibration delivered to the tissue. The value of the Fourier transform 142 of the deformation at this particular frequency fq is a complex number whose argument is the phase delay $\varphi$ (in radians). The phase delay $\varphi$ may then be converted into a time, before being plotted against depth d. A linear curve fit 144 may be superimposed to the phase delay graph 143 obtained in this way, so that the operator can more easily assess tissue homogeneity (by checking that the phase delay does not depart significantly from a linear variation).

The amplitude Amp of the variation of the tissue deformation over time (that is to say the amplitude of the envelope of this variation), at a given depth d, can be determined in the same way as for the phase delay, but considering the amplitude of the Fourier transform at the peak frequency fq, instead of its phase, for example. The amplitude Amp could also be determined using another kind of amplitude envelope estimation or detection technique.

When the tissue 51 is homogeneous and suitable for elastic wave propagation, the amplitude Amp is expected to vary with depth d according to a given theoretical model, for instance proportionally to $1/d^n$, where n is an integer comprised between 1 and 3. To enable the operator to easily check whether the amplitude Amp varies with depth in this manner, the amplitude Amp can be plotted against depth using a log-linear scale. Indeed, when such a scale is used, the graph representing the variations of the amplitude over depth is linear, which can be readily assessed from a visual point of view, should the amplitude vary proportionally to $1/d^n$.

The homogeneity indicator 810 can be displayed in the form of a binary indicator, like a green/red or green/black one, or in a more gradual manner, in the form of a needle dial, a percentage value, or a level bar (like a kind of progress bar), for instance.

The homogeneity indicator 810 specifies whether the tissue 51 is homogeneous, more precisely homogeneous over the given depth range mentioned above, and suitable for the propagation of elastic wave, or not. The homogeneity indicator 810 may specify this information either in a binary, all-or-nothing manner, or in a more gradual way, as a continuous value.

By way of illustration, when the homogeneity indicator provides this information in a binary manner, if the tip of the probe is placed in contact with the surface of a phantom (that is a test sample made of a synthetic viscoelastic material) that is homogeneous, deprived of air or liquid inclusions or interpositions, large enough (at least 10 cm wide and 10 cm deep), and that has a Young's modulus comprised between 1 and 100 kilopascals (or, alternatively, comprised between 5 and 75 kilopascals), then, the indicator specifies (for instance by turning to green) that the medium is homogeneous and suitable for the propagation of elastic waves. And if the phantom is not homogeneous (for instance, includes hard beads), or comprises a water layer a few centimeters below its surface, then the indicator specifies that the medium is not homogeneous or not suitable for the propagation of elastic waves (for instance by turning to black).

The control module 21 can be programmed to determine the homogeneity indicator by processing the periodic elastic wave propagation image 808 in order to detect the presence of one or more homogeneous diagonal stripes in this image. When such stripes are detected, the homogeneity indicator 810 indicates, for instance by switching from black to green, that the tissue 51 is homogeneous and suitable for the propagation of elastic wave.

The control module 21 can also be programmed to determine the homogeneity indicator by processing the periodic elastic wave propagation image 808 to detect an edge or an average line of such a stripe, and to determine, by linear curve fitting, whether this edge or line is substantially linear over the range of depth of interest and/or has a slope comprised in a given interval of likely values. The substantially linear nature of this line or edge can be assessed based on a fitting quality parameter, like the coefficient of determination $R^2$, the standard deviation or other tools giving the adequacy between the fitted line and a strictly linear variation over depth. The control module may be programmed to determine that this line or edge is substantially linear when the coefficient of determination $R^2$ is higher than or equal to 0.8, or even higher than or equal to 0.9, for example. The homogeneity indicator could be determined as being equal, or proportional to this fitting quality parameter.

The control module 21 can also be programmed to determine the homogeneity indicator by determining whether the phase delay $\varphi$ varies substantially linearly with depth over the range of depth of interest and/or has a slope comprised in a given interval of likely values. This determination can be carried on by linear curve fitting, as explained above.

The control module 21 can also be programmed to determine the homogeneity indicator by determining whether the phase delay $\varphi$ varies substantially linearly with depth over the range of depth of interest and/or has a slope comprised in a given interval of likely values. This determination can be carried on by linear curve fitting, as described above.

The control module 21 can also be programmed to determine the homogeneity indicator by determining whether the amplitude Amp varies with depth according to a given model or not, in particular whether the amplitude Amp is proportionally to $1/d^n$ or not. This determination can be carried on by curve fitting. The fact the amplitude Amp varies with depth according to the model can be assessed based on a fitting quality parameter, like the determination coefficient $R^2$ giving the adequation between the variations of the amplitude over depth and the model. The homogeneity indicator could be determined as being equal, or proportional to this fitting quality parameter.

The control module 21 can also be programmed to determine different intermediary homogeneity indicators, based on the different the criteria describes above (so, determined either from the periodic elastic wave propagation image 808, from the variations of the phase delay, or from the variations of the amplitude Amp), and to determine then a final homogeneity indicator based on these different intermediary homogeneity indicators, for instance by averaging theses intermediary homogeneity indicators.

The control module 21 can also be programmed to estimate, in step c1), a preliminary value of a mechanical property of the tissue related to shear wave propagation, such as its Young's modulus, or a range of values in which this mechanical property is likely to be found. This value or range of value is determined from the data representative of the periodic deformation of the tissue determined in step c0). This value or range of value is then provided to the operator, by means of the display screen of the operator interface 30, for instance.

To this end, the control module 21 may derive a preliminary estimate of the propagation speed of shear waves in the tissue, from the slope of the diagonal stripes of the periodic elastic wave propagation image 808 described above, or from the slope of the line 404 representing the variations of the phase delay $\varphi$ over depth d. The control module 21 may then determine a preliminary estimate of the Young's modulus, from this value of the propagation speed of shear waves. As mentioned in preamble, a value of the propagation speed of shear waves determined in this way is usually less accurate than a value determined by transient elastography (due to compression and shear wave superposition, inter alia). But it is still useful for the operator to be provided with such a preliminary value, or range of values in which the actual value of the Young's modulus (or other mechanical property of the tissue) is likely to be found.

Step S1: Measuring Tissue Stiffness by Transient Elastography

In step S1, to determine the mechanical property of the tissue 51 related to shear wave propagation (e.g.: shear modulus, Young's modulus E, shear wave speed, . . . ) by transient elastography, the control module 21 is programmed to make the system 1 executing the following steps:

d) stopping the continuous and periodic mechanical vibration PMV, then delivering a transient low frequency mechanical pulse to the tissue of the subject;

e) emitting a sequence of ultrasound shots by means of the ultrasound emitter 11 and acquiring corresponding echo signals received by the ultrasound receiver 11, while the low frequency mechanical pulse travels through the tissue 51;

f) determining said mechanical property of the tissue related to shear wave propagation, from at least some of the echo signals acquired in step f).

The control module 21 may be more specifically programmed in order to, in step f):

f0) determine, from the echo signals acquired in step e), data representative of a transient deformation of the tissue, at different depths within the tissue and at different times after the low frequency mechanical pulse was delivered to the tissue; and to f1) determine the mechanical property of the tissue related to shear wave propagation, from the data representative of the transient deformation of the tissue determined in step f0).

In step d), the control module 21 controls the vibrator 12 (via the motion actuation servo controller 23) so that it delivers to the tissue the transient mechanical pulse, whose duration is typically smaller than 0.2 second (the pulse duration is understood to mean the time laps, outside of which the pulse amplitude is smaller than one tenth of the peak, maximum amplitude of the pulse). This mechanical pulse is a low frequency one in that its spectral content (its spectral density) is mostly locate below 500 hertz, or even below 100 hertz. The pulse duration is typically smaller than 10/f, or even smaller than 2/f, where f is the central frequency of the pulse spectrum.

In step e), the control module 21 may control the ultrasound transducer 11 (via the ultrasonic transmitter module 27) so that it emits the sequence of ultrasound shots at a pulse repetition rate higher than or equal to 2 kilohertz. The ultrasound shots emitted are similar to the ones emitted in step b) of step S0. But they are emitted at a higher pulse repetition rate, as step S1 is for precisely measuring the mechanical property of the tissue, not just for visualizing, monitoring tissue homogeneity.

For example, the transient mechanical pulse may last for 20 or 40 milliseconds, the sequence of ultrasound shots last 80 milliseconds and the ultrasound shots be emitted at a pulse repetition rate of 6 kilohertz, thus enabling to track the deformation of the tissue as a function of depth at 480 different successive instants distributed during this 80 milliseconds period (that starts when the emission of the transient mechanical pulse starts). In other words, in this case, the transient elastic wave propagation image 805 would comprise 480 columns.

In step f0), the data representative of the transient deformation of the tissue are determined by comparing the echo signals acquired in step e) one with each other, for instance using a correlation technique or another patterning matching algorithm, like in step c0) of step S0.

In step f1), the mechanical property of the tissue, related to shear wave propagation, is determined according to techniques known in the art.

The control module 21 may be programmed in order to, in step f1), provide a transient elastic wave propagation image, like the image 805 of FIG. 15, representing the deformation of the tissue caused by the transient mechanical pulse, both as a function of depth and as a function of time, so that the operator can visually check the quality of the transient elastography measurement.

Figure 1:
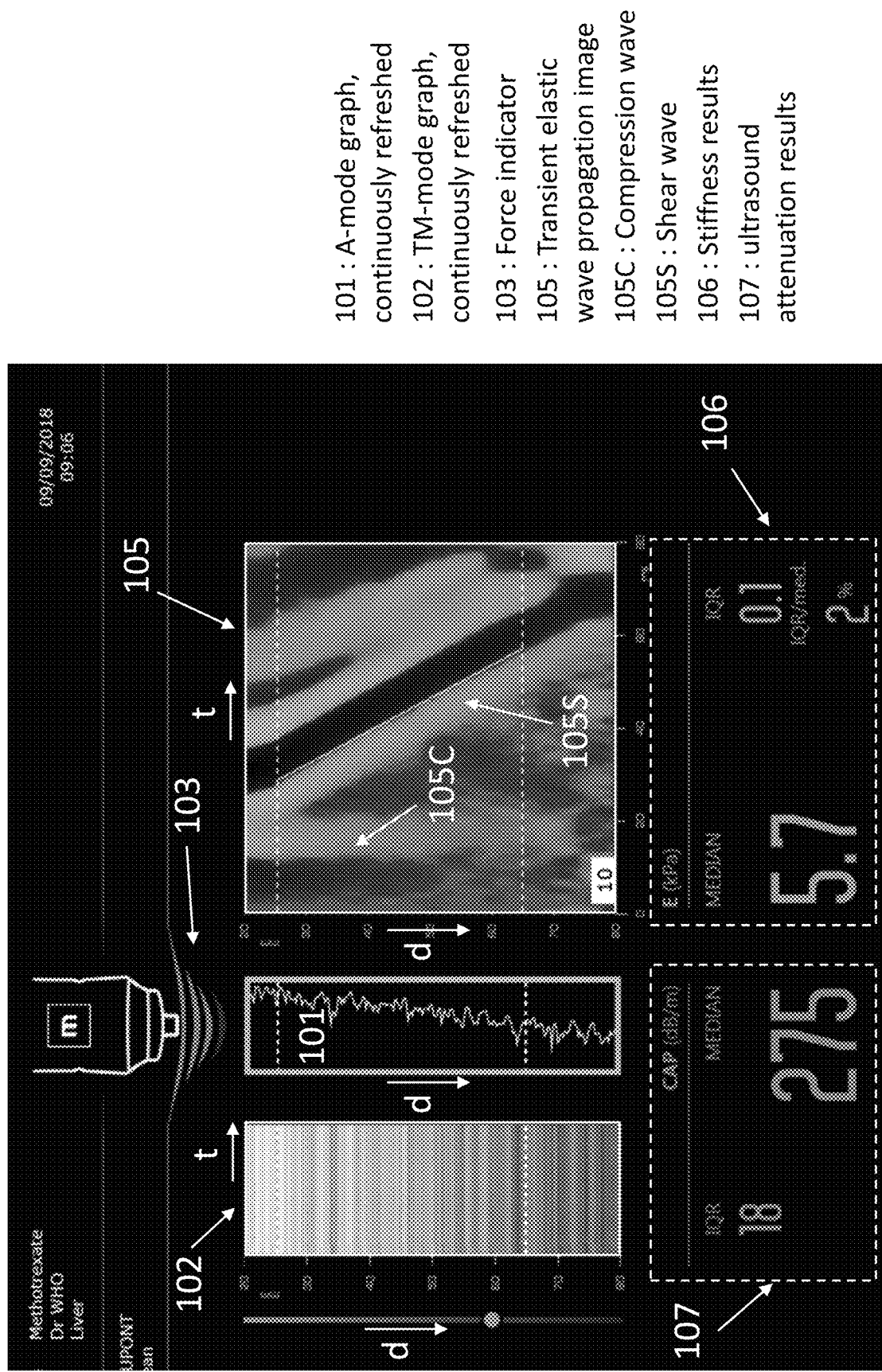
FIG. 1 shows different graphs and indicators displayed to an operator by means of a display screen of a FIBROSCAN® system.
Figure 4:
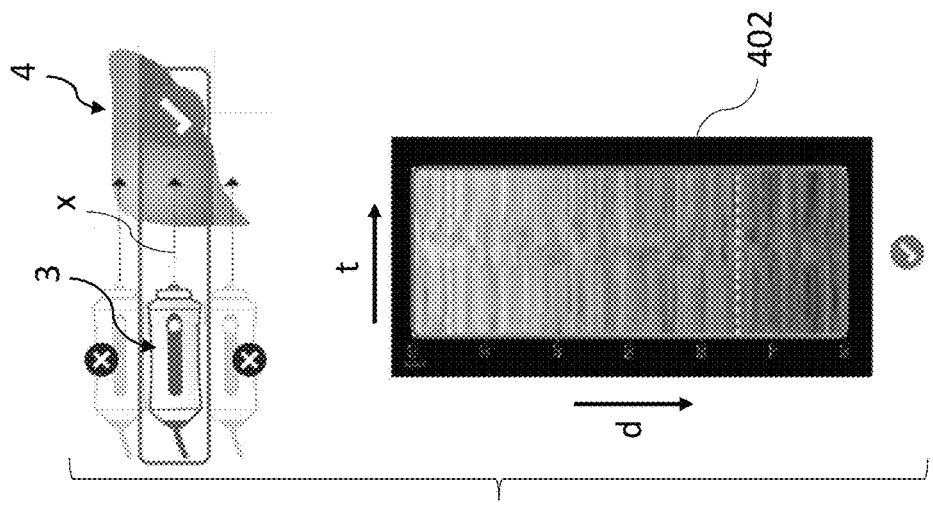
FIGS. 2 to 4 show different TM-mode graphs, displayed to an operator for different positions of a FIBROSCAN®'s probe with respect to an organ to be characterized.
Figure 3:
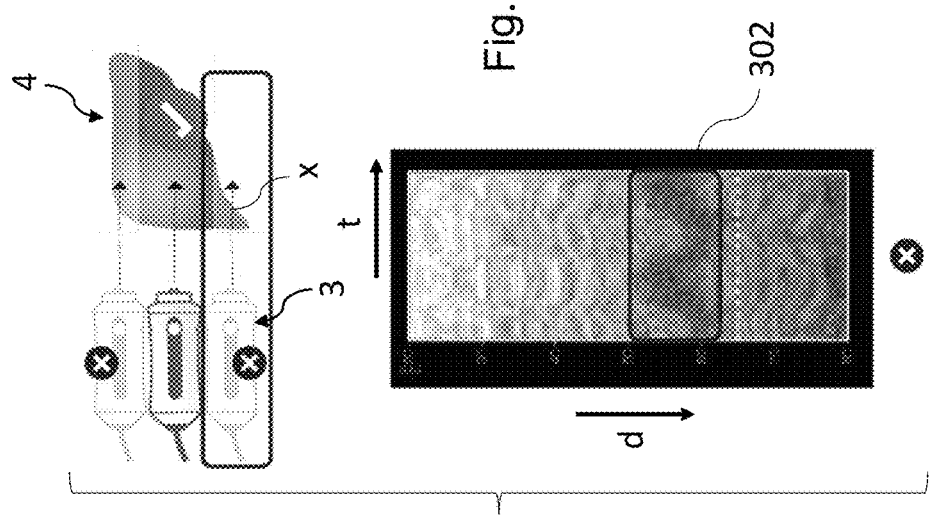
Figure 2:
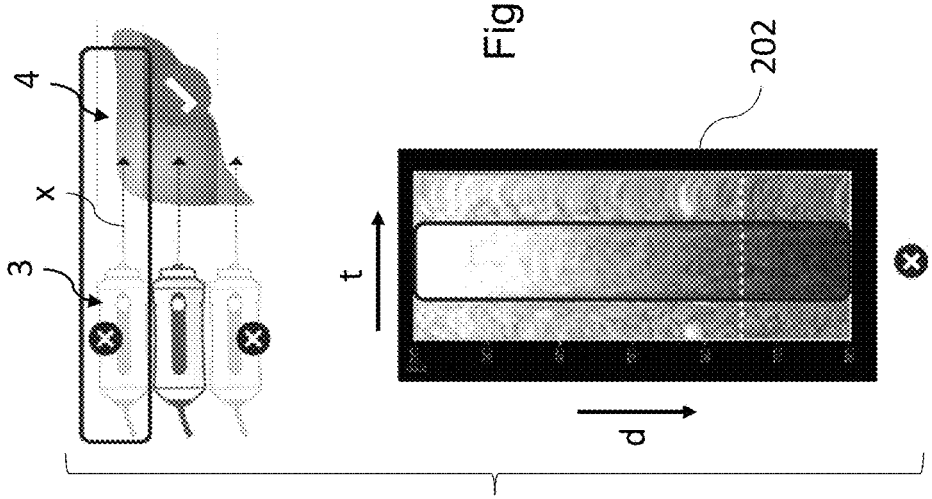

The control module 21 may also be programmed to provide the operator with the value of the mechanical property of the tissue, once determined, for instance in the form of the stiffness results display 106 shown in FIG. 1.

Step S2: Providing an Ultrasound Attenuation Value to the Operator

In step S2, the control module 12 provides the operator 40 with a value of the ultrasound attenuation parameter mentioned above, for instance by displaying this value on the screen 31 of the operator interface (e.g.: in the form of the attenuation results display 107 of FIG. 1).

The ultrasound attenuation parameter is determined by the control module 21 from some or all of the echo signals acquired in step b) of step S0, more precisely during the last execution of step b), just before So stops. This calculation can be achieved either in step S0, or only once executing step S2, that is to say once the operator has actuated the manual trigger.

One may remark that a number of variations may be made in the method for characterizing tissue presented above without departing from the scope of the disclosed technology.

For instance, step S2 could be suppressed (the method then comprising step S0 and step S1, but not S2). Similarly, step S1 could be suppressed.

Besides, the transition from Step S0, to step S1 and/or S2, could be triggered automatically, by the control module itself, when the homogeneity indicator described above indicates that the tissue under examination is homogeneous and suitable for elastic wave propagation.

The method could also comprise step S0 only, the step of providing the ultrasound attenuation parameter to the operator being executed within step S0, regardless of the more or less homogeneous nature of the tissue under examination. Still, in such a case, the control module may be programmed to determine a quality coefficient associated to the ultrasound attenuation parameter, this quality coefficient being all the higher as the tissue is homogeneous with respect to the propagation of the periodic mechanical vibration delivered to the tissue. This quality coefficient could be determined on the basis of the homogeneity indicator described above, for instance as being equal or proportional to the value of this indicator.

The different operations executed during the method could be organized in steps according to a different distribution than the one presented above (in particular, the method could thus comprise a greater number of steps or sub-steps).

The disclosed technology provides also a non-transitory computer readable medium comprising a computer program comprising machine executable instructions whose execution by a control module of a system comprising a probe, to be hold against the body of a subject and that comprises a vibrator to deliver mechanical vibrations to a tissue of the subject an ultrasound emitter configured to emit a sequence of ultrasound shots and an ultrasound receiver configured to receive corresponding echo signals makes the control module to execute the following steps:

a) controlling the probe so that it delivers a continuous and periodic mechanical vibration to the tissue of the subject;

b) controlling the ultrasound emitter so that it emits a sequence of ultrasound shots and acquiring corresponding echo signals received by the ultrasound receiver, to track how the tissue is moved by the periodic mechanical vibration delivered to the tissue;

c) providing homogeneity information to an operator of the system, the homogeneity information the homogeneity information being determined from at least some of the echo signals acquired in step b), the homogeneity information being representative of the ability of the tissue to transmit elastic waves and of the homogeneity of the tissue with respect to the propagation of elastic waves; steps b) and c) being executed continuously, several times successively.

Embodiments of the subject matter and the operations or steps described in this specification (e.g. the elements of the central unit 20 of FIG. 7) can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "control module" encompasses all kinds of apparatus, devices, and machines for processing data, including by way of example a microprocessor, a digital signal processor (DSP), a computer, a system on a chip, or multiple ones, or combinations of the foregoing. The control module can include special purpose logic circuitry (like in the case of FIG. 1) e.g., an FPGA or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A system for characterizing tissue, comprising:
a probe, to be held against the body of a subject and that comprises a vibrator to deliver mechanical vibrations to a tissue of the subject;
an ultrasound emitter that is configured to emit a sequence of ultrasound shots and an ultrasound receiver configured to receive corresponding echo signals; and
a control module programmed to make the system execute the following steps:
  a) delivering a continuous and periodic mechanical vibration to the tissue of the subject, the periodic mechanical vibration comprising of a same vibration pattern repeated several times successively over time;
  b) emitting a sequence of ultrasound shots by means of the ultrasound emitter and acquiring corresponding echo signals received by the ultrasound receiver to track how the tissue is moved by the periodic mechanical vibration delivered to the tissue;
  c) providing homogeneity information to an operator of the system, the homogeneity information being determined from at least some of the echo signals acquired in step b) and by carrying out a comparison between said at least some echo signals acquired in step b), the homogeneity information being representative of the ability of the tissue to transmit elastic waves and of the homogeneity of the tissue with respect to the propagation of elastic waves, and said homogeneity information being determined independently of a stiffness measurement of said tissue such that the at least some of the echo signals that are processed by the control module to provide homogeneity information of said tissue are different from echo signals that are processed for making the stiffness measurement of said tissue; and d) carrying out the stiffness measurement, the control module being programmed so that steps b) and c) are executed by the system continuously, several times successively while the continuous and periodic mechanical vibration is delivered to the tissue.

2. The system of claim 1, wherein the control module is further programmed to determine at least one physical property of the tissue comprising one of:
an ultrasound parameter, relative to ultrasound wave propagation within the tissue;
a mechanical property of the tissue related to shear wave propagation, determined by transient elastography.

3. The system of claim 2 wherein, the control module being programmed to determine said mechanical property of the tissue related to shear wave propagation, by transient elastography, the control module is further programmed to make the system executing the following steps to carry out the stiffness measurement:
d1) stopping the continuous and periodic mechanical vibration, then delivering a transient low frequency mechanical pulse to the tissue of the subject;
e) emitting a sequence of ultrasound shots by means of the ultrasound emitter and acquiring corresponding echo signals received by the ultrasound receiver, while the low frequency mechanical pulse travels through the tissue;
f) determining said mechanical property of the tissue related to shear wave propagation, from at least some of the echo signals acquired in step e).

4. The system of claim 3, wherein the control module is programmed to trigger the execution of steps d1), e) and f):
when a manual trigger is actuated by the operator of the system; or
automatically, when said homogeneity information indicates that the tissue is homogeneous with respect to respect to the propagation of the periodic mechanical vibration delivered to the tissue.

5. The system of claim 2, wherein the control module is further programmed to determine said ultrasound parameter provided that the homogeneity information indicates that the tissue is homogeneous with respect to the propagation of elastic waves, and wherein said ultrasound parameter is determined from one or more of the echo signals acquired in step b).

6. The system of claim 2, wherein the control module is programmed to determine said ultrasound parameter from one or more of the echo signals acquired in step b), and to determine a quality coefficient associated to said ultrasound parameter, the quality coefficient being all the higher as the tissue is homogeneous with respect to the propagation of elastic waves.

7. The system of claim 1, wherein the control module is programmed to determine, from at least some of the echo signals acquired in step b), data representative of a periodic deformation of the tissue, at different depths within the tissue and at different moments of the periodic mechanical vibration delivered to the tissue, and wherein said homogeneity information comprises one of the following:
a graph representing the variation over depth of at least one temporal characteristic of the temporal, periodic variation of the deformation of the tissue; or
an indication specifying whether said characteristic varies with depth as if the tissue were homogeneous over a given range of depth, or not.

8. The system of claim 7, wherein:
said graph represents the deformation of the tissue at different depths within the tissue and at different moments of the periodic mechanical vibration delivered to the tissue, said graph being a two-dimensional image whose pixels row index represents depth and whose pixels column index represents time, or conversely, each pixel having a pixel value representing the deformation of the tissue at the depth and time associated to the pixel considered; or wherein
said indication specifies whether said graph, which represents the deformation of the tissue at different depths within the tissue and at different moments of the periodic mechanical vibration delivered to the tissue, said graph being a two-dimensional image whose pixels row index represents depth and whose pixels column index represents time or conversely, each pixel having a pixel value representing the deformation of the tissue at the depth and time associated to the pixel considered, is comprised of diagonal stripes over said range of depth, or not.

9. The system of claim 7, wherein:
said graph represents a phase delay of the periodic deformation of the tissue, as a function of depth; or wherein
said indication specifies whether the phase delay of the periodic deformation of the tissue varies substantially linearly with depth over said range of depth, or not.

10. The system of claim 1, wherein the control module is programmed so that the sequence of ultrasound shots emitted in step b) spans at least over one half of a same period of the periodic mechanical vibration delivered to the tissue, and comprises at least 10 ultrasound shots per period of said mechanical vibration.

11. The system of claim 1, wherein the control module is programmed so that:
a base frequency of the periodic mechanical vibration delivered to the tissue of the subject is comprised between 10 hertz and 200 hertz, and
in step b), the ultrasound shots are emitted at a pulse repetition rate higher than or equal to 500 hertz.

12. The system of claim 3, wherein the control module is programmed so that, in step e), the ultrasound shots are emitted at a pulse repetition rate higher than or equal to 2 kilohertz.

13. The system of claim 1, wherein the control module is programmed so that the system executes the set of steps comprising steps b) and c) in real time.

14. The system of claim 1, wherein:
the homogeneity information provided to the operator comprises a graph representing a deformation of the tissue, at different depths within the tissue and at different moments of the periodic mechanical vibration delivered to the tissue, and wherein
the control module is programmed so that the emission of the sequence of ultrasound shots of step b) is synchronized with the periodic mechanical vibration, the sequence of ultrasound shots starting from an instant which, within a cycle of the periodic mechanical vibration delivered to the tissue, is the same for each execution of step b).

15. The system of claim 1, wherein the homogeneity information provided to the operator in step c) comprises a graph representing a deformation of the tissue, both as a function of depth and as a function of time, the graph starting from an instant which, within a period of the periodic mechanical vibration delivered to the tissue, is the same each time the graph is updated on the base of newly determined deformation data.

16. The system of claim 1, wherein the probe's vibrator is rotationally symmetrical around a vibrator axis, and wherein the ultrasound emitter and the ultrasound receiver are constituted by a same ultrasound transducer that is rotationally symmetrical around a transducer axis that coincide with the vibrator axis.

17. The system of claim 1, wherein the control module is programmed to:
determine, from at least some of the echo signals acquired in step b), data representative of a periodic deformation of the tissue, at different depths within the tissue and at different moments of the periodic mechanical vibration delivered to the tissue; and to
estimate a value of a mechanical property of the tissue related to shear wave propagation, or a range of values in which a mechanical property of the tissue related to shear wave propagation is likely to be found, based on said data.

18. The system of claim 1:
further comprising a manual adjustment control for adjusting an amplitude of the periodic mechanical vibration, the control module being further programmed to provide to the operator an information representative of an amplitude of a periodic deformation of the tissue, caused by the periodic mechanical vibration delivered to the tissue, the amplitude of periodic deformation of the tissue being determined from at least some of the echo signals acquired in step b), or
wherein the control module is programmed to adjust automatically the amplitude of the periodic mechanical vibration delivered to the subject based on the amplitude of the periodic deformation of the tissue.

19. A method comprising characterizing a tissue, carried on by means of a system comprising:
a probe, to be held against the skin of a subject and that comprises a vibrator to deliver mechanical vibrations to a tissue of a subject;
an ultrasound emitter that is configured to emit a sequence of ultrasound shots and an ultrasound receiver that is configured to receive corresponding echo signals; and
a control module programmed to make the system execute the following steps:
a) delivering a continuous and periodic mechanical vibration to the tissue of the subject, the periodic mechanical vibration comprising of a same vibration pattern repeated several times successively over time;
b) emitting a sequence of ultrasound shots by means of the ultrasound emitter and acquiring corresponding echo signals received by the ultrasound receiver to track how the tissue is moved by the periodic mechanical vibration delivered to the tissue;
c) providing homogeneity information to an operator of the system, the homogeneity information being determined from at least some of the echo signals acquired in step b) and by carrying out a comparison between said at least some echo signals acquired in step b), the homogeneity information being representative of the ability of the tissue to transmit elastic waves and of the homogeneity of the tissue with respect to the propagation of elastic waves, and said homogeneity information being determined independently of a stiffness measurement of said tissue such that the at least some of the echo signals that are processed by the control module to provide homogeneity information of said tissue are different from echo signals that are processed for making the stiffness measurement of said tissue; and
d) carrying out the stiffness measurement,
the control module being programmed so that steps b) and c) are executed by the system continuously, several times successively while the continuous and periodic mechanical vibration is delivered to the tissue.

20. The method of claim 19, further comprising a determination of at least one physical property of the tissue comprising one of:
an ultrasound parameter, relative to ultrasound wave propagation within the tissue;
a mechanical property of the tissue related to shear wave propagation, determined by transient elastography.

21. The method of claim 19, comprising a determination, from at least some of the echo signals acquired in step b), of data representative of a periodic deformation of the tissue, at different depths within the tissue and at different moments of the periodic mechanical vibration delivered to the tissue, and wherein said homogeneity information comprises one of the following:
a graph representing the variation over depth of at least one temporal characteristic of the temporal, periodic variation of the deformation of the tissue; or
an indication specifying whether said characteristic varies with depth as if the tissue were homogeneous over a given range of depth, or not.

22. The method of claim 21, wherein:
said graph represents the deformation of the tissue at different depths within the tissue and at different moments of the periodic mechanical vibration delivered to the tissue, said graph being a two-dimensional image whose pixels row index represents depth and whose pixels column index represents time, or conversely, each pixel having a pixel value representing the deformation of the tissue at the depth and time associated to the pixel considered; or wherein
said indication specifies whether said graph, which represents the deformation of the tissue at different depths within the tissue and at different moments of the periodic mechanical vibration delivered to the tissue, said graph being a two-dimensional image whose pixels row index represents depth and whose pixels column index represents time or conversely, each pixel having a pixel value representing the deformation of the tissue at the depth and time associated to the pixel considered, is comprised of diagonal stripes over said range of depth, or not.

* * * * *